(12) United States Patent
Shitara et al.

(10) Patent No.: US 6,617,160 B1
(45) Date of Patent: Sep. 9, 2003

(54) ANTI-HUMAN VEGF RECEPTOR FLT-1 MONOCLONAL ANTIBODY

(75) Inventors: Kenya Shitara, Fujisawa (JP); Mikito Ito, Machida (JP); Nobuo Hanai, Sagamihara (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/119,014

(22) Filed: Jul. 20, 1998

Related U.S. Application Data

(63) Continuation-in-part of application No. PCT/JP97/04259, filed on Nov. 21, 1997.

(30) Foreign Application Priority Data

Nov. 21, 1996 (JP) .............................................. 8-311109

(51) Int. Cl.$^7$ .............................................. C07K 16/24
(52) U.S. Cl. ................ 435/335; 530/388.1; 530/388.23
(58) Field of Search .......................... 530/387.9, 388.1, 530/388.22, 388.23, 350, 351; 435/7.1, 335; 424/138.1, 139.1, 141.1, 143.1, 144.1

(56) References Cited

U.S. PATENT DOCUMENTS

| | | | |
|---|---|---|---|
| 5,750,078 A | 5/1998 | Shitara et al. | |
| 5,807,548 A | 9/1998 | Shitara et al. | |
| 5,830,470 A | 11/1998 | Nakamura et al. | |
| 5,840,301 A | * 11/1998 | Rockwell et al. | ......... 424/143.1 |
| 5,866,692 A | 2/1999 | Shitara et al. | |
| 5,874,255 A | 2/1999 | Nakamura et al. | |
| 5,874,542 A | 2/1999 | Rockwell et al. | |
| 5,942,385 A | * 8/1999 | Hirth | ............................. 435/4 |
| 6,100,071 A | * 8/2000 | Davis-Smyth et al. | |

FOREIGN PATENT DOCUMENTS

| | | |
|---|---|---|
| EP | 0 882 799 A1 | 12/1998 |
| WO | WO 95 21868 | 8/1995 |

OTHER PUBLICATIONS

Seetharam et al., "A unique signal transduction from FLT tyrosine kinase, a receptor for vascular endothelial factor VEGF", Oncogene (1995) 10, 135–147.

Kim et al., Inhibition of vascular endothelial growth factor-induced angiogenesis suppresses tumour growth in vi Nature, vol. 362, Apr. 29, 1993, pp. 841–844.

De Vries et al., "The fms–Like Tyrosine Kinase, a Receptor for Vascular Endothelial Growth Factor", Reports, Feb. 21, 1992, pp. 989–991.

Melnyk et al., "Vascular Endothelial Growth Factor Promotes Tumor Dissemination by a Mechanism Distinct Effect on Primary Tumor Growth", Cancer Research 56, pp. 921–924, Feb. 15, 1996.

Folkman et al., "Minireview: Angiogenesis", The Journal of Biological Chemistry, vol. 267, No. 16, Issue of pp. 10931–10934, 1992.

Senger et al., Tumor Cells Secrete a Vascular Permeability Factor That Promotes Accumulation of Ascites Flu Science, vol. 219, Feb. 25, 1983, pp. 983–985.

Ferrara et al., "Pituitary Follicular Cells Secrete A Novel Heparin–Binding Growth Factor Specific For Vascul Endothelial Cells", Biochemical and Biophysical Research Communications, vol. 161, No. 2, 1989, Jun. 15, 198 851–858.

Leung et al., "Vascular Endothelial Growth Factor is a Secreted Angiogenic Mitogen", Science, pp. 1306–1309, 1989.

Koch et al., "Vascular Endothelial Growth Factor A Cytokine Modulating Endothelial Function in Rheumatoid Arthritis", Journal of Immunology, 1994, 152: 4149–4156.

Unemori et al., "Vascular Endothelial Growth Factor Induces Intersitial Collagenase Expression in Human End Cells", Journal of Cellular Physiology 153: 557–562 (1992).

Pepper et al., "Vascular Endothelial Growth Factor (VEGF) Induces Plasminogen Activators and Plasminogen Activator Inhibitor–1 in Microvascular Endothelial Cells", Biochemical and Biophysical Research Communicatio 181, No. 2, 1991, Dec. 16, 1991, pp. 902–906.

Asahara et al., "Synergistic Effect of Vascular Endothelial Growth Factor and Basic Fibroblast Growth Factor Angiogeneis In Vivo", Basic Research, Supplement II, Circulation, vol. 92, No. 9, Nov. 1, 1995, pp. 365–371.

Houck et al., "Dual Regulation of Vascular Endothelial Growth Factor Bioavailability by Genetic and Proteolyt Mechanisms", The Journal of Biological Chemistry, vol. 267, No. 36, Dec. 25, 1992, pp. 26031–26037.

Takahashi et al., "Markedly Increased Amounts of Messenger RNAs for Vascular Endothelial Growth Factor Placenta Growth Factor in Renal Cell Carcinoma Associated with Angiogenesis", Cancer Research 54, 4233–4237 Aug. 1, 1994.

Berkman et al., "Expression of the Vascular Permeability Factor/Vascular Endothelial Growth Factor Gene in Nervous System Neoplasms", The Journal of Clinical Investigation, Inc., vol. 91, Jan. 1993, pp. 153–159.

Brown et al., "Expression of Vascular Permeability Factor (Vascular Endothelial Growth Factor) and Its Recept Adenocarcinomas of the Gastrointestinal Tract", Cancer Research 53, 4727–4735, Oct. 1, 1993.

(List continued on next page.)

*Primary Examiner*—Lorraine Spector
(74) *Attorney, Agent, or Firm*—Nixon & Vanderhye, P.C.

(57) ABSTRACT

The present invention provides a monoclonal antibody which immunologically reacts with human VEGF receptor Flt-1 and cells in which human VEGF receptor Flt-1 is expressed on the cell surface and a monoclonal antibody which inhibits binding of human VEGF to human VEGF receptor Flt-1. It also provides a means for the diagnosis or treatment of diseases in which their morbid states progress by abnormal angiogensis, such as proliferation or metastasis of solid tumors, arthritis in rheumatoid, arthritis, diabetic retinopathy, retinopathy of prematurity, psoriasis, and the like.

10 Claims, 12 Drawing Sheets

OTHER PUBLICATIONS

Olson et al., "Vascular Permeability Factor Gene Expression in Normal and Neoplastic Human Ovaries", Cancer Research 54, 276–280, Jan. 1, 1994.

Toi et al., "Association of Vascular Endothelial Growth Factor Expression with Tumor Angiogenesis and with Early Relapse Breast Cancer", Jpn. J. Cancer Res., 85, 1045–1049, Oct. 1994.

Kondo et al., "Vascular Endothelial Growth Factor/Vascular Permeability Factor is Detectable in the Sera of Tumor–Bearing Mice and Cancer Patients", Biochimica et Biophysica Acta 1221 (1994) pp. 211–214.

Aiello et al., "Vascular Endothelial Growth Factor in Ocular Fluid of Patients with Diabetic Retinopathy and Other Retinal Disorders", The New England Journal of Medicine, vol. 331, No. 22, pp. 1480–1487, Dec. 1, 1994.

Fava et al., "Vascular Permeability Factor/Endothelial Growth Factor (VPE/VEGF): Accumulation and Expression i Human Synovial Fluids and Rheumatoid Synovial Tissue", J. Exp. Med., vol. 180, Jul. 1994, pp. 341–346.

Matthews et al., "A Receptor Tyrosine Kinase cDNA Isolated from a Population of Enriched Primitive Hematopoietic Cells and Exhibiting Close Genetic Linkage to c–kit", Proc. Natl. Acad. Sci. USA, vol. 88, pp. 9026–9030, Oct. 1991 Biochemistry.

Terman et al., "Identification of the KDR Tyrosine Kinase as a Receptor for Vascular Endothelial Cell Growth Factor", Biochemical and Biophysical Research Communications, vol. 187, No. 3, 1992, pp. 1579–1586, Sep. 30, 1992.

Quinn et al., "Fetal Liver Kinase 1 is a Receptor for Vascular Endothelial Growth Factor and is Selectively Expressed in Vascular Endothelium", Proc. Natl. Acad. Sci. USA, vol. 90, pp. 7533–7537, Aug. 1993 Cell Biology.

Peters et al., "Vascular Endothelial Growth Factor Receptor Expression During Embryogenesis and Tissue Repair Suggests a Role in Endothelial Differentiation and Blood Vessel Growth", Proc. Natl. Acad. Sci. USA, vol. 90, pp. 8915–8919, Oct. 1993 Developmental Biology.

Plate et al., "Vascular Endothelial Growth Factor is a Potential Tumour Angiogenesis Factor in Human Gliomas In Vivo", Nature, vol. 359, Oct. 29, 1992, pp. 845–848.

Fong et al., "Role of the Flt–1 Receptor Tyrosine Kinase in Regulating the Assembly of Vascular Endothelium", Nature, vol. 376, Jul. 6, 1995, pp. 66–70.

Sawano et al., "Flt–1 But Not KDR/Flk–1 Tyrosin Kinase Is a Receptor for Placenta Growth Factor, Which is Related to Vascular Endothelial Growth Factor", Cell Growth & Differentiation, vol. 7, pp. 213–221, Feb. 1996.

Hanai et al., "Detailed Characterization of Reactivities of Anti–Gastric Cancer Monoclonal Antibodies to Carbohydrate Antigen", Anticancer Research 10: 1579–1586.

Hanai et al., "Generation of Monoclonal Antibodies Against Human Lung Squamous Cell Carcinoma and Adenocarcinoma Using Mice Rendered Tolerant to Normal Human Lung", Cancer Research 46, 4438–4443, Sep. 1986.

Shitara et al., "Application of Anti Lung Adenocarcinoma Monoclonal Antibody Recognizing Cytokeratin–Like Cytoplasmic Antigen for Tumor Diagnosis", Anticancer Research 12: 1121–1130 (1992).

Bird, et al, "Single–Chain Antigen–Binding Proteins", Science, vol. 242, Oct. 1988, pp. 423–426.

Mitola et al, "Tat–Human Immunodeficiency Virus–1 Induces Human Monocyte Chemotaxis by Activation of Vascular Endothelial Growth Factor Receptor–1". Blood, vol. 90, No. 4 (Aug. 15, 1997, pp 1365–1372).

Webber et al, "Preparation and Characterization of a Disulfide–Stabilized Fv Fragment of the Anti–TAC Antibody: Comparison with its Single–Chain Analog", Molecular Immunology, vol. 32, No. 4, pp. 249–258, 1995.

Shibuya, "Role of VEGF–FLT Receptor System in Normal and Tumor Angiogenesis", Advances in Cancer Research, vol. 67, Institute of Medical Science, University of Tokyo, Copyright 1995, pp. 281–316.

Davis–Smyth et al, EMBO Journal, vol. 15, No. 18, 1996, pp. 4919–4927.

Tanaka, et al., Characterization of the Extracellular Domain in Vascular Endothelial Growth Factor Receptor–1 (Flt–1 Tyrosine Kinase), Sep. 1997, Jpn J. Cancer Research, 88, pp. 867–876.

Wiesmann, et al., Crystal Structure at 1.7 Å Resolution of VEGF in Complex with Domain 2 of the Flt–1 Receptor, Nov. 28, 1997, Cell, vol. 91, pp. 694–704.

* cited by examiner

ANTI-HUMAN VEGF RECEPTOR FLT-1 MONOCLONAL ANTIBODY

CROSS-REFERENCE TO RELATED APPLICATION

This is a continuation-in-part application of PCT/JP97/04259 filed on Nov. 21, 1997.

BACKGROUND OF THE INVENTION

1. Field of the Invention

This invention relates to a monoclonal antibody capable of specifically binding to human VEGF receptor Flt-1 which is useful the diagnosis or treatment of diseases in which their morbid states progress by abnormal angiogenesis, such as proliferation or metastasis of solid tumors, arthritis in rheumatoid arthritis, diabetic retinopathy, retinopathy of prematurity and psoriasis; a hybridoma capable of producing the antibody; a method for immunologically detecting human VEGF receptor Flt-1 using the monoclonal antibody; and a diagnostic method and a therapeutic method for diseases, such as solid tumor, rheumatoid arthritis, diabetic retinopathy, retinopathy of prematurity, psoriasis and the like, using the monoclonal antibody.

2. Brief Description of the Background Art

Angiogensis plays an important role in the individual development and construction of tissues in vertebrates, is directly involved in the formation of the corpus luteum during the sexual cycle, transient proliferation of the uterine endometrium and formation of the placenta in mature individuals (females). With regard to pathological states, angiogenesis is involved in the proliferation or metastasis of solid tumors and formation or acceleration of morbidity in diabetic retinopathy and rheumatoid arthritis (*J. Biol. Chem.*, 267, 10931 (1992). Angiogenesis occurs by the secretion of an angiogenesis factor and involves process of a tube formation and producing a new blood vessel. During this process, the basement membrane and interstitum are destroyed by a protease secreted from endothelial cells of an existing blood vessel around the secreted angiogenesis factor, followed by subsequent wandering and proliferation of vascular endothelial cells (*J. Biol. Chem.*, 267, 10931, (1992)). Factors which induce angiogenesis include vascular permeability factor (hereinafter "VPF") and vascular endothelial growth factor (hereinafter "VEGF") (hereinafter "VPF/VEGF"). These factors are considered the most important factors in pathological and non-pathological angiogenesis (*Advances in Cancer Research*, 67, 281 (1995)). VPF/VEGF is a protein having a molecular weight of about 40,000 constituted by homodimers, which had been reported to be independent molecules as vascular permeability factor (VPF) in 1983 (*Science*, 219, 983 (1993)) and as vascular endothelial growth factor (VEGF) in 1989 (*Biochem. Biophys. Res. Comm.*, 161, 851 (1989)), but it has been revealed as the results of cDNA cloning that they are the same substance (*Science*, 246, 1306 (1989); *Science* 246, 1309 (1989)) (hereinafter, the term "VPF/VEGF" is recited as "VEGF"). Beyond the activity of VEGF upon vascular endothelial cells described above, VEGF has also been shown to have a growth enhancing activity (*Biochem. Biophys. Res. Comm.*, 161, 851 (1989)), a migration enhancing activity (*J. Immunology*, 152, 4149 (1994)), a metalloprotease secretion enhancing activity (*J. Cell Physiol.*, 153, 557 (1992)), a urokinase and tPA secretion enhancing activity (*Biochem, Biophys. Res. Comm.*, 181, 902 (1991)), and the like. Furthermore, VEGF has been shown to have an angiogenesis enhancing activity (*Circulation*, 92 suppl II, 365 (1995)), a vascular permeability enhancing activity (*Science*, 219, 983 (1983)), and the like as its in vivo activities. It has been reported that VEGF is a growth factor having extremely high specificity for vascular endothelial cells (*Biochem. Biophys. Res. Comm.*, 161, 851 (1989)) and that four proteins having different molecular weight are present due to alternative splicing of mRNA (*J. Biol. Chem.*, 267, 26031 (1991)).

Among diseases accomplished by angiogenesis, it has been reported that VEGF plays an important role in the proliferation or metastasis of solid tumors and formation of morbid states of diabetic retinopathy and rheumatiod arthritis. With regard to solid tumors, production of VEGF in a number of human tumor tissues has been reported, such as in renal carcinoma (*Cancer Research*, 54, 4233 (1994)), breast cancer (*Human Pathology*, 26, 86 (1995)), brain tumor (*J. Clinical Investigation*, 91, 153 (1993)), gastrointestinal cancer (*Cancer Research*, 53, 4727 (1993)), ovarian cancer (*Cancer Research*, 54, 276 (1994)), and the like. Also, results of a study on the correlation between VEGF expression quantity in tumors and survival ratio of patients in patients with breast cancer have revealed that tumor angiogenesis is more active in tumors expressing high levels of VEGF than low VEGF expression tumors and that the survival ratio is lower in breast cancer patients having high VEGF expression tumors than breast cancer patients having low VEGF expression tumors (*Japanese J. Cancer Research*, 85, 1045 (1994)). It has been reported also that an anti-VEGF monoclonal antibody inhibited tumor growth in a xenograft model test system in which a human tumor was transferred into nude mice by subcutaneous transplantation (*Nature*, 362, 841 (1993)). Also, it has been reported that, in a metastatic cancer model of a human tumor in nude mice, an anti-VEGF monoclonal antibody inhibited metastasis of the tumor (*Cancer Research*, 56, 921 (1996)). Additionally, since a high concentration of VEGF was detected in human carcinomatous pleural perfusions and ascites, the possibility that VEGF is a major factor involved in the retention of pleural perfusions and ascites has been suggested (*Biochimica et Biophysica Acta*, 1221, 211 (1944)).

In diabetic retinopathy, abnormal angiogenesis causes retinal detachment and hemorrhage of the vitreous body, resulting in blindness, and it has been reported that angiogenesis in diabetic retinopathy and the expression level of VEGF in the patient's eye balls are positively correlative (*New England J. Medicine*, 331, 1480 (1994)). Also, it has been reported that angiogenesis in a monkey retinopathy model is inhibited when the VEGF activity is inhibited by the intraocular administration of an anti-VEGF neutralizing monoclonal antibody (*Arch. Ophthalmol.*, 114, 66 (1996)).

Progress in the morbid states of rheumatoid arthritis (destruction of bone and cartilage) is accompanied by angiogenesis, and it has been reported that a high concentration of VEGF is contained in the synovial fluid of patients with rheumatoid arthritis and that macrophages in joints of patients with rheumatoid produce VEGF rheumatoid arthritis (*Journal of Immunology*, 152, 4149 (1994); *J. Experimental Medicine*, 180, 341 (1994)).

VEGF receptors have been reported. These include fms-like tyrosine kinase (referred to as "Flt-1" hereinafter) (*Oncogene*, 5, 519 (1990); *Science*, 255, 989 (1992)) and kinase insert domain-containing receptor (referred to as "KDR" hereinafter) (WO 92/14748; *Proc. Natl. Acad. Sci., USA*, 88, 9026 (1992); *Biochem. Biophys. Res. Comm.* 187, 1579 (1992); WO 94/11499), which belong to the receptor type tyrosine kinase family. Each of Flt-1 and KDR is a membrane protein of 180 to 200 kilodalton in molecular weight which has an extracellular domain consisting of 7 immunoglobulin-like regions and an intracellular domain consisting of a tyrosine kinase region. It has been reported that VEGF specifically binds to Flt-1 and KDR at Kd values of 20 pM and 75 pM and that Flt-1 and KDR are expressed in vascular endothelial cells in a specific manner (*Proc. Natl. Acad. Sci., USA*, 90, 7533 (1993); *Proc. Natl. Acad. Sci., USA*, 90, 8915 (1993)). With regard to Flt-1 in various diseases, it has been reported that, in comparison with vascular endothelial cells in normal tissues, expression of Flt-1 mRNA increases in tumor vascular endothelial cells of human glioblastoma tissues (*Nature*, 349, 845 (1992)) and tumor vascular endothelial cells of human digestive organ cancer tissues (*Cancer Research*, 53, 4727 (1993)). Additionally, it has been reported that expression of Flt-1 mRNA is observed by in situ hybridization in vascular endothelial cells of joints of patients with rheumatoid arthritis (*J. Experimental Medicine*, 180, 341 (1994)). These results strongly suggest that a VEGF/VEGF receptor Flt-1 system plays an important role in tumor angiogenesis. Although it has been reported that VEGF binds to Flt-1 and the intracellular domain is auto-phosphorylated (*Science*, 255, 989 (1992)), the detailed function of the receptor mechanism is still unclear. However, it has been discovered that knock out mice which the Flt-1 gene was destroyed die after a fetal age of 8.5 to 9.5 days due to abnormal blood vessel construction caused by abnormal morphology of vascular endothelial cells during blood island formation in the early stage of development and subsequent angiogenesis. This had led to an assumption that Flt-1 has a function essential for the tube formation of vascular endothelial cells in angiogenesis (*Nature*, 376, 66 (1995)).

In view of the above, it is expected that an antibody which can inhibit biological activities of VEGF through its binding to VEGF receptor Flt-1 will be useful for the diagnosis or treatment of diseases in which their morbid states progress by abnormal angiogenesis, such as proliferation or metastasis of solid tumors, arthritis in rheumatoid arthritis, diabetic retinopathy, retinopathy of prematurity and psoriasis. However, an anti-VEGF receptor Flt-1 monoclonal antibody which can detect cells in which VEGF receptor Flt-1 is expressed and anti-VEGF receptor Flt-1 monoclonal antibody which can inhibit biological activities of VEGF has not been described in the art.

SUMMARY OF THE INVENTION

Concern has been described toward the development of a method which is useful for the diagnosis or treatment of diseases in which their morbid states progress by abnormal angiogenesis, such as proliferation or metastasis of solid tumors, arthritis in rheumatoid arthritis, diabetic retinopathy, retinopathy of prematurity and psoriasis. Although nothing has been reported on the anti-human VEGF receptor Flt-1 monoclonal antibody, it is considered that detection of the regions of angiogenesis and inhibition of angiogenesis by the use of an anti-human VEGF receptor Flt-1 monoclonal antibody will be useful for the diagnosis and treatment of these diseases.

The present invention relates to a monoclonal antibody which specifically reacts with human VEGF receptor Flt-1; a monoclonal antibody which recognizes an epitope present in a region of amino acids 1 to 750, especially 1 to 338, of the N-terminal sequence of human VEGF receptor Flt-1 signal and receptor protein; (SEQ ID NO: 5 and 6) a monoclonal antibody which specifically reacts with human VEGF receptor Flt-1 by immunocyte staining; and a monoclonal antibody which inhibits binding of human VEGF to human VEGF receptor Flt-1 and inhibits biological activities of human VEGF.

Furthermore, the present invention relates to monoclonal antibody KM1730 belonging to mouse IgG1 subclass produced by hybridoma KM1730 (FERM BP-5697); monoclonal antibody KM1731 belonging to mouse IgG2a subclass produced by hybridoma KM1731 (FERM BP-5718); monoclonal antibody KM1732 belonging to mouse IgG1 subclass produced by hybridoma KM1732 (FERM BP-5698); monoclonal antibody KM1748 belonging to mouse IgG2b subclass produced by hybridoma KM1748 (FERM BP-5699); and monoclonal antibody KM1750 belonging to mouse IgG2b subclass produced by hybridoma KM1750 (FERM BP-5700).

Moreover, the present invention relates to hybridoma KM1730 (FERM BP-5697) which produces monoclonal antibody KM1730; hybridoma KM1731 (FERM BP-5718) which produces monoclonal antibody KM1731; hybridoma KM1732 (FERM BP-5698) which produces monoclonal antibody KM1732; hybridoma KM1748 (FERM BP-5699) which produces monoclonal antibody of KM1748; and hybridoma KM1750 (FERM BP-5700) which produces monoclonal antibody KM1750.

Also, the present invention relates to a method for detecting a disease in which the morbid states progress by abnormal angiogenesis, comprising the steps of: (a) separating human cell or a crushing solution thereof, tissue or a crushing solution thereof, serum, pleural fluid, ascites fluid, or ocular fluid to prepare a sample, (b) reacting the separated sample prepared in the step (a) with the monoclonal antibody of the present invention, (c) further reacting the reacted sample prepared in the step (b) with a labeled anti-mouse IgG antibody or binding fragment, and (d) measuring or observing the labeled sample prepared in the step (c); a method for immunologically detecting human VEGF receptor Flt-1, comprising the step of reacting the human VEGF receptor Flt-1 with the monoclonal antibody of the present invention; a method for immunologically detecting cells in which human VEGF receptor Flt-1 is expressed on the surface thereof, comprising the step of reacting the human VEGF receptor Flt-1 with the monoclonal antibody of the present invention; and a method for detecting and determining soluble human VEGF receptor Flt-1, comprising the step of reacting the human VEGF receptor Flt-1 with the monoclonal antibody of the present invention.

Still furthermore, the present invention relates to a method for preventing or treating a disease, comprising the step of administering to human or animal in need of such prevention or treatment an effective amount of the monoclonal antibody of the present invention; a method for inhibiting binding the human VEGF to human VEGF receptor Flt-1, comprising the step of reacting the human VEGF receptor Flt-1 with the monoclonal antibody of the present invention; and a method for inhibiting biological activities of human VEGF, comprising the step of reacting human VEGF receptor Flt-1 with the monoclonal antibody of the present invention.

Still moreover, the present invention relates to a composition comprising the monoclonal antibody of the present invention and a diagnostic or pharmaceutical acceptable carrier.

DETAILED DESCRIPTION OF THE INVENTION

Figure 1:
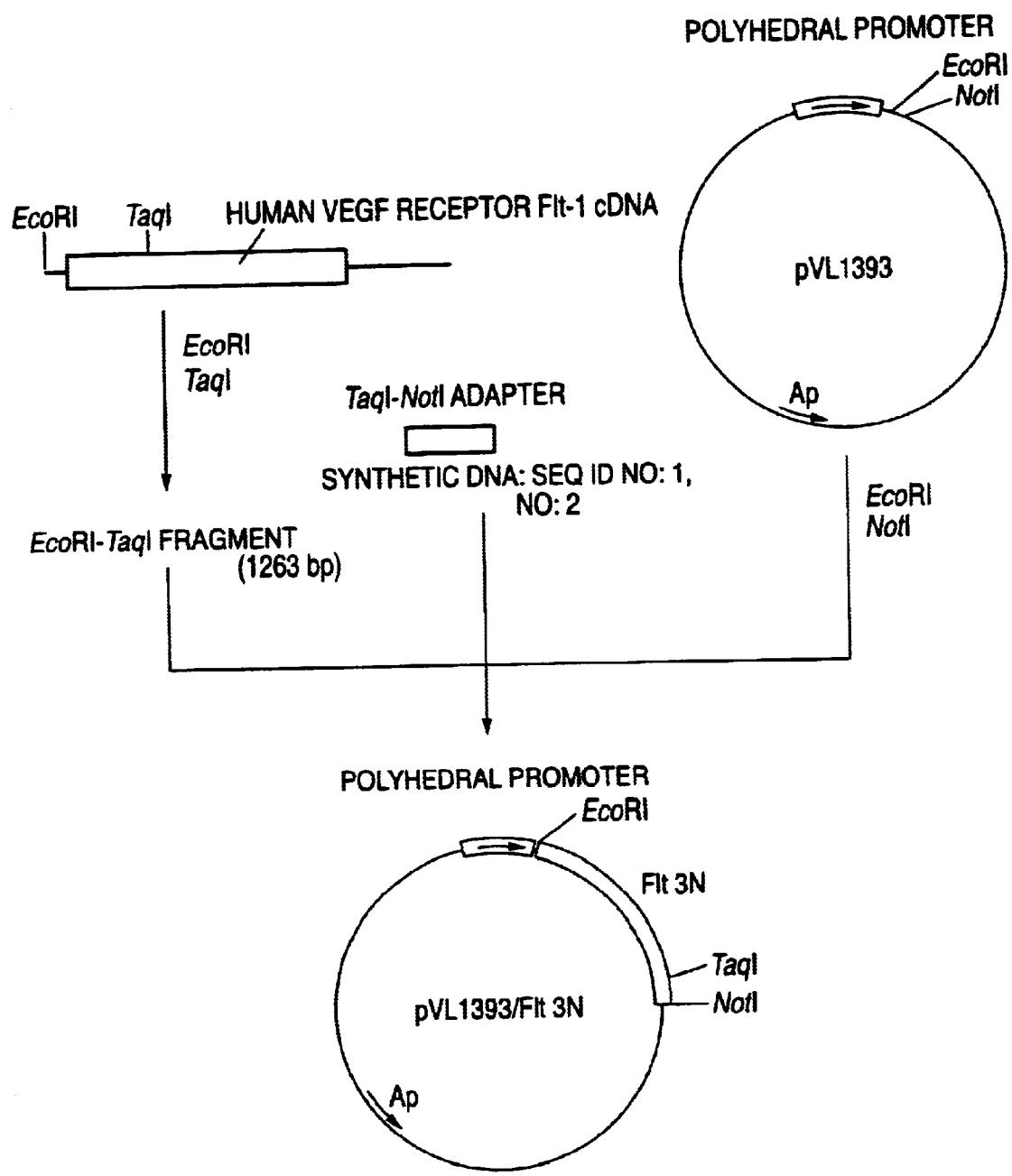
FIG. 1 is a graph showing construction steps of plasmid pVL1393/Flt 3N.

The present invention relates to a diagnostic agent of diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

The invention of the present invention have found that anti-human VEGF receptor Flt-1 monoclonal antibody capable of recognizing an epitope present in a region of the 1st to 750th positions for the N-terminal amino acid of human VEGF receptor Flt-1 can specifically react with the human VEGF receptor Flt-1 by immunocyte staining, and that biological activities of human VEGF can be inhibited by the inhibition of binding the VEGF to VEGF receptor Flt-1. Diagnosis and treatment of the above-described diseases in which their morbid states progress by abnormal angiogenesis, such as proliferation or metastasis of solid tumors, arthritis in rheumatoid arthritis, diabetic retinopathy, prematurity retinopathy and psoriasis, can be carried out by using these monoclonal antibodies.

Consequently, the present invention provides antibodies which specifically react with human VEGF receptor Flt-1. With regard to the monoclonal antibody of the present invention, a monoclonal antibody is provided that recognizes an epitope which is present in a region of the 1st to 750th positions from the N-terminal amino acid (including a signal sequence) of human VEGF receptor Flt-1, particularly an epitope which is present in a region of the 1st to 338th positions from the N-terminal amino acid (including a signal sequence of human VEGF receptor Flt-1, and also specifically reacts with human VEGF receptor Flt-1 by immunocyte staining. Also, the present invention provides a monoclonal antibody which inhibits binding of human VEGF to human VEGF receptor Flt-1 and also inhibits biological activities of the human VEGF. Examples of the monoclonal antibody which recognizes the epitope and also specifically reacts with human VEGF receptor Flt-1 by immunocyte staining include monoclonal antibody KM1730 produced by the hybridoma KM1730 (FERM BP-5697), monoclonal antibody KM1731 produced by the hybridoma KM1731 (FERM BP-5718), monoclonal antibody KM1732 produced by the hybridoma KM1732 (FERM BP-5698), monoclonal antibody KM1748 produced by the hybridoma KM1748 (FERM BP-5699), and monoclonal antibody KM1750 produced by the hybridoma KM1750 (FERM BP-5700). Examples of the monoclonal antibody which inhibits binding of human VEGF to human VEGF receptor Flt-1 and also inhibits biological activities of human VEGF include monoclonal antibody KM1732 produced by the hybridoma KM1732 (FERM BP-5698), monoclonal antibody KM1748 produced by the hybridoma KM1748 (FERM BP-5699), and monoclonal antibody KM1750 produced by the hybridoma KM1750 (FERM BP-5700).

The monoclonal antibody of the present invention may be any antibody, so long as it specifically reacts with human VEGF receptor Flt-1, but those which are established by the following production method can be cited as preferred examples. That is, anti-human VEGF receptor Flt-1 monoclonal antibody can be obtained by preparing human VEGF receptor Flt-1 protein as an antigen, immunizing an animal capable of providing a hybridoma with the antigen, such as mouse, rat, hamster, rabbit or the like, thereby inducing plasma cells having the antigen specificity, preparing a hybridoma capable of producing the monoclonal antibody through fusion of the cells with a myelmoa cell line and subsequently culturing the hybridoma.

The production method of the anti-human VEGF receptor Flt-1 antibody of the present invention is described below.

1. Production method of anti-human VEGF receptor Flt-1 monoclonal antibody (1) Preparation of antigen Examples of the substance useful as the antigen for the preparation of the anti-human VEGF receptor Flt-1 monoclonal antibody include cells in which human VEGF receptor Flt-1 is expressed on the cell surface or a cell membrane fraction thereof, soluble human VEGF receptor Flt-1 protein having an extracellular region of different length and a fusion protein of the protein with Fc region of the antibody. As the cells capable of expressing human VEGF receptor Flt-1 on the cell surface, NIH3T3-Flt-1 cells (*Oncogene*, 10, 135 (1995)) can be exemplified. In a method for expressing the antigen as soluble human VEGF receptor Flt-1 protein having an extracellular region of different length or a fusion protein of the protein with Fc region of the antibody, the whole length or a partial fragment of cDNA which encodes human VEGF receptor Flt-1 (*Oncogene*, 5, 519 (1990); *Abstract of Papers, the 18th Annual meeting of Japan Molecular Biology Society*, 2P-227 (December 1995)) is inserted into a downstream site of the promoter of an appropriate vector, the thus constructed recombinant vector is inserted into host cells and the thus obtained human VEGF receptor Flt-1 expression cells are cultured in an appropriate medium, thereby producing the whole length of a partial fragment of human VEGF receptor Flt-1 in the cells or culture supernatant as such or as a fusion protein.

As the host cells, any one of bacteria, yeast, animal cells, insect cells and the like can be used so long as they can express the gene of interest. Examples of the bacteria include the genus Escherichia, the genus Bacillus and the like, such as *Escherichia coli, Bacillus subtilis* and the like. Examples of the yeast include *Saccharomyces cerevisiae, Schizosaccharomyces pompe* and the like. Examples of the animal cells include namalwa cells which are human cells, COS cells which are monkey cells and CHO cells which are Chinese hamster cells. Examples of the insect cells include Sf9 and Sf21 (produced by Pharmingen), High Five (produced by Invitrogen) and the like.

When a bacterium such as *Escherichia coli* is used as the host, the expression vector may be preferably constructed with a promoter, a ribosome binding sequence, the DNA of the present invention, a transcription termination sequence and, as occasion demands, a promoter controlling sequence. Examples include commercially available pGEX (produced by Pharmacia), pET System (produced by Novagen) and the like.

With regard to the method for introducing the recombinant vector into a bacterium, any one of the known methods for introducing DNA into bacteria, such as a method in which calcium ion is used (*Proc. Natl. Acad. Sci., USA*, 69, 2110–2114 (1972)), a protoplast method (Japanese Published Unexamined Patent Application No. 2483942/91), and the like can be used.

When yeast is used as the host, YEp13 (ATCC 37115), YEp24 (ATCC 37051), YCp50 (ATCC 37419), or the like is used as the expression vector.

With regard to the method for introducing the recombinant vector into yeast, any one of the known methods for introducing DNA into yeast, such as an electroporation method (*Methods. Enzymol.*, 194, 182–187 (1990)), a spheroplast method (*Proc. Natl. Acad. Sci., USA*, 84, 1929–1933 (1978)), a lithium acetate method (*J. Bacteriol.*, 153, 163–168 (1983)), and the like can be used.

When animal cells are used as the host, pAGE107 (Japanese Published Unexamined Patent Application No. 22979/88; *Cytotechnology*, 3, 133 (1990)), pAGE103 (*J. Biochem.*, 101, 1307 (1987)), and the like can be exemplified as the useful expression vector.

Any promoter capable of effecting the expression in animal cells can be used. Examples include the promoter of IE (immediate early) gene of cytomegalovirus (CMV), the SV40 promoter, the metallothionein promoter and the like. Furthermore, the enhancer of the IE gene of human CMV may be used together with the promoter.

With regard to the method for the introduction of the recombinant vector into animal cells, any one of the known methods for introducing DNA into animal cells, such as an electroporation method (*Cytotechnology*, 3, 135 (1990)), a calcium phosphate method (Japanese Published Unexamined Patent Application No. 227075/90), a lipofection method (*Proc. Natl. Acad. Sci., USA*, 84, 7413, (1987)) and the like can be used.

When insect cells are used as the host, the protein can be expressed by the known method described in, for example, *Current Protocols in Molecular Biology*, Supplement 1-34 and Baculovirus expression vectors, A laboratory manual. That is, the recombinant gene introducing vector and baculovirus described in the following are simultaneously introduced into insect cells to obtain a recombinant virus in the insect cell cultures supernatant and then the insect cells are infected with the thus obtained recombinant virus to obtain protein-expressing insect cells.

Examples of the gene introducing vector include pVL1392, pVL1393, pBlueBacIII (all manufactured by Invitrogen), and the like.

Examples of the baculovirus include Autograph californica nuclear polyhedrosis virus with which insects of the family Barathra are infected.

With regard to the method for the simultaneous introduction of the above-described recombinant gene introducing vector and the above-described baculovirus into insect cells for the preparation of the recombinant virus, calcium, phosphate method (Japanese Published Unexamined Patent Application No. 227075/90), lipofection method (*Proc. Natl. Acad. Sci., USA*, 84, 7413 (1987)) and the like can be exemplified.

Alternatively, the protein of interest can be produced by preparing a recombinant baculovirus making use, for example, of BaculoGold Starter Kit manufactured by Pharmigen and then infecting the above-described insect cells, such as Sf9, Sf21, High Five, or the like, with the recombinant virus (*Bio/Technology*, 6, 47 (1988)).

With regard to the gene expression method, techniques, such as secretion production, fusion protein expression and the like have been developed, and each of these every methods can be used. For example, gene expression can be produced in accordance with the method described in *Molecular Cloning 2nd edition*, Cold Spring Harbor Lab. Press, New York (1989), or by direct expression.

The whole length or a partial fragment of a human VEGF receptor Flt-1 can be produced as such or as a fusion protein thereof by culturing a transformant obtained in the above-described manner in a culture medium, thereby effecting formation and accumulation of the protein of the present invention in the resulting culture mixture, and then collecting the protein from the culture mixture.

Culturing of the transformant of the present invention in a culture medium is carried out in accordance with a usual method which is used in the culturing of respective host cells.

With regard to the medium for use in the culturing of the transformant obtained using a microorganism, such as *Escherichia coli*, yeast, or the like, as the host, either a natural medium or a synthetic medium may be used, so long as it contains materials which can be assimilated by the microorganism, such as carbon sources, nitrogen sources, inorganic salts, and the like, and can perform culturing of the transformant efficiently (*Molecular Cloning* 2nd edition, Cold Spring Harbor Lab. Press, New York (1989)). The culturing is carried out generally under aerobic conditions, such as a shaking culture, submerged agitation aeration culture, or the like, at 15 to 40° C. for 16 to 96 hours. During the culturing, the pH is controlled to 3.0 to 9.0. Adjustment of the pH is carried out using an inorganic or organic acid, an akali solution, urea, calcium carbonate, ammonia, and the like. As occasion demands, antibiotics, such as ampicillin, tetracycline, and the like may be added to the medium during the culturing.

With regard to the medium for use in the culturing of a transformant obtained using animal cells as the best, RPMI 1640 medium, Eagle's MEM medium or any one of these media further supplemented with fetal calf serum may be used. The culturing is carried out generally at 35 to 37° C. for 3 to 7 days in the presence of 5% $Co_2$. As occasion demands, antibiotics, such as kanamycin, penicillin, and the like may be added to the medium during the culturing.

With regarding to the medium for use in the culturing of a transformant obtained using insect cells as the host, TNM-FH medium (produced by Pharmingen), Sf900IISFM (produced by Life Technologies), ExCell400 or ExCell405 (both produced by JRH Biosciences), or the like may be used. The culturing is carried out generally at 25 to 30° C. for 1 to 4 days, and gentamicin and the like antibiotics may be added to the medium during the culturing as occasion demands.

Although media for the culturing of animal cells and insect cells contain serum, it is desirable to use a serum-free medium in order to efficiently purify the whole length or a partial fragment of human VEGF receptor Flt-1 as such or as a fusion protein.

When the whole length or a partial fragment of human VEGF receptor Flt-1 is accumulated inside the host cells as such or as a fusion protein, the cells after completion of the culturing are collected by centrifugation, suspended in an aqueous buffer and then disrupted using ultrasonic oscillator, French press, or the like, and subsequently collecting the protein from a supernatant fluid prepared by centrifuging the thus disrupted cells.

Also, when an insoluble body is formed inside the cells, the insoluble body is solubilized using a protein denaturing agent and then higher-order structure of the protein is formed by diluting or dialyzing the thus solubilized protein in or against a solution which does not contain the protein denaturing agent or contains the agent but in such a low concentration that the protein is not denatured.

When the whole length or a partial fragment of human VEGF receptor Flt-1 is secreted outside the cells as such or as a fusion protein, the expressed protein can be collected from the culture supernatant. The isolation and purification can be carried out by employing separation means, such as solvent extraction, fractional precipitation with organic solvents, salting out, dialysis, centrifugation, ultracentrifugation, ion exchange chromatography, gel filtration chromatography, hydrophobic chromatography, affinity chromatography, reverse phase chromatography, crystallization, electrophoresis, and the like, alone or in combination.

(2) Immunization of animals and preparation of antibody producing cells

Although any one of animals, such as mice, rats, hamsters, rabbits, and the like, can be used in the immunization, so long as a hybridoma can be prepared, an example in which mice and rats are used is described in this invention. A mouse or rat of 3 to 20 weeks of age is immunized with the protein obtained in the above step 1-(1) as the antigen, and antibody producing cells are collected from the spleen, lymph node or peripheral blood of the animal. The immunization is carried out by administering the antigen several times through subcutaneous, intravenous or intraperitoneal injection together with an appropriate adjuvant. As the adjuvant, a complete Freund's adjuvant or a combination of aluminum hydroxide gel with pertussis vaccine can be exemplified. A blood sample is collected from the fundus of the eye or caudal vein of the animal 3 to 7 days after each administration, the sample is tested, for example, by enzyme immunoassay ((Enzyme-linked Immunosorbent Assay (ELISA), published by Igaku Shoin, (1976)) as to whether it is reactive with the antigen used, namely soluble human VEGF receptor Flt-1 or NIH3T3 cells in which human VEGF receptor Flt-1 is expressed on the cell surface, and then a mouse or rat showing sufficient antibody titer in their sera is submitted for use as the supply source of antibody producing cells. On the 3rd to 7th day after final administration of the antigen, the spleen is excised from the immunized mouse or rat to carry out fusion of the spleen cells with myeloma cells in accordance with the known method (*Antibodies—A Laboratory Manual,* Cold Spring Harbor Laboratory, (1988); referred to as "*Antibodies—A Laboratory Manual*" hereinafter).

(3) Preparation of myeloma cells

As the myeloma cells, any myeloma cells capable of growing in vitro may be used, which include established cells obtained from mouse, such as 8-asaguanine-resistant mouse (BALB/c) myeloma cell lines P3-X63Ag8-U1 (G. Kohler et al., *Europ. J. Immunol,* 6, 511 (1976)), SP2/0-Ag14 (SP-21 (M. Shulman et al., *Nature,* 265, 269 (1978)), P3-X63-Ag8653 (653) (J. F. Kearney et al., *J. Immunol.,* 123, 1548 (1979)), P3-X63-Ag8 (X63) (G. Kohler et al., *Nature,* 256, 495 (1975)), and the like. These cell lines are cultured and subcultured in accordance with the known method (*Antibodies—A Laboratory Manual*) and $2 \times 10^7$ or more of the cells are secured until cell fusion.

(4) Cell fusion

The antibody producing cells obtained in the above step (2) and the myeloma cells obtained in the above step ( 3) are washed, mixed with cell aggregating medium, polyethylene glycol-1000 (PEG-1000) or the like, to effect cell fusion and then suspended in a culture medium. For the washing of the cells, MEM medium or PBS (1.83 g of disodium hydrogen phosphate, 0.21 g of potassium dihydrogen phosphate, 7.65 g of sodium chloride, 1 liter of distilled water, pH 7.2) is used. In order to obtain the fused cells of interest selectively, HAT medium {normal medium (a medium prepared by adding glutamine (1.5 mM), 2-mercaptoethanol ($5 \times 10^{-5}$ M), gentamicin (10 μg/ml) and fetal calf serum (FCS) (10%, produced by CSL) to RPMI-1640 medium) further supplemented with hypoxanthine ($10^{-4}$ M), thymidine ($1.5 \times 10^{-5}$ M) and aminopterin ($4 \times 10^{-7}$ M)} is used as the medium for suspending the fused cells.

After the culturing, a portion of the culture supernatant is sampled and tested, for example, by an enzyme immunoassay method which will be described in the following step (5) to select wells which can specifically react with human VEGF receptor Flt-1 or a recombinant protein such as a fusion protein with human VEGF receptor Flt-1 described in the above step (1). Thereafter, cloning is carried out twice by limiting dilution analysis (using HT medium (a medium prepared by eliminating aminopterin from the HAT medium) for the first analysis and the normal medium for the second analysis), and a hybridoma which shows stable and high antibody titer is selected as the hybridoma capable of producing the anti-human VEGF receptor Flt-1 monoclonal antibody.

(5) Selection of anti-human VEGF receptor Flt-1 monoclonal antibody

Selection of a hybridoma capable of producing the anti-human VEGF receptor Flt-1 monoclonal antibody is carried out by the enzyme immunoassay method described below.

Enzyme immunoassay

Human VEGF receptor Flt-1 or a recombinant protein such as a fusion protein with the human VEGF receptor Flt-1 described in the above step (1-(1) is coated on an appropriate plate and allowed to react with a first antibody, namely a hybridoma culture supernatant or a purified antibody obtained in the following step 1-(6), and then with a second antibody, namely an anti-mouse immunoglobulin antibody or anti-rat immunoglobulin antibody labeled with biotin, an enzyme, a chemiluminescent substance, a radioactive compound or the like, and then a reaction suitable for the label used is carried out in order to select a sample which specifically reacts with human VEGF receptor Flt-1 as a hybridoma capable of producing anti-human VEGF receptor Flt-1 monoclonal antibody. Examples of the hybridoma include hybridomas KM1730, KM1731, KM1732, KM1748 and KM1750. The hybridomas KM1730, KM1732, KM1748 and KM1750, on Oct. 8, 1996, and the hybridoma KM1731, on Oct. 22, 1996, were deposited with National Institute of Bioscience and Human Technology, Agency of Industrial Science and Technology (Higashi 1-1-3, Tsukuba-shi, Ibaraki, Japan), and were assigned the designations as FERM BP-5697, FERM BP-5698, FERM BP-5699, FERM BP-5700 and FERM BP-5718, respectively.

(6) Preparation of monoclonal antibody

The anti-human VEGF receptor Flt-1 monoclonal antibody-producing hybridoma cells obtained in the above-described step 1-(3) are administered by intraperitoneal injection into 8- to 10-week-old mice or nude mice treated with pristane (by intraperitoneal administration of 0.5 ml of 2,6,10,14-tetramethylpentadecane (pristane) followed by 2 weeks of feeding) at a dose of $2 \times 10^7$ to $5 \times 10^6$ cells/animal. The hybridoma causes ascites tumor in 10 to 21 days. The ascitic fluid is collected from the mice or nude mice, centrifuged, subjected to salting out with 40 to 50% saturated ammonium sulfate or to caprylic acid precipitation and then passed through a DEAE-Sepharose column, protein A column or Cellulofine GSL 2000 (produced by Seikagaku Kogyo) to collect an IgG or IgM fraction to give a purified monoclonal antibody.

The subclass of the purified monoclonal antibody can be determined using a mouse monoclonal antibody typing kit or a rat monoclonal antibody typing kit. The amount of protein can be determined by the Lowry method or by calculation based on the optical density at 280 nm.

Furthermore, the present invention relates to, using the monoclonal antibody of the present invention, a method for immunologically detecting human VEGF receptor Flt-1 or cells in which human VEGF receptor Flt-1 is expressed on the surface thereof, a method for immunologically detecting and determining soluble human VEGF receptor Flt-1, and a method for inhibiting binding of a human VEGF to human VEGF receptor Flt-1 or biological activities of human VEGF.

Moreover, the present invention relates to a diagnostic agent for diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

The method for detecting and determining human VEGF receptor Flt-1 are described below.

2. Detection and determination of human VEGF receptor Flt-1 using anti-human VEGF receptor Flt-1 monoclonal antibody The method for detecting a disease in which the morbid states progress by abnormal angiogenesis includes a fluorescent antibody method, an enzyme-linked immunosorbent assay (ELISA), a radioactive material labeled immunoassay (RIA), an immunocyte staining method, an immunotissue staining method, Western blotting method, an immunoprecipitation method, and the like.

The fluorescent antibody method comprises the steps of: (a) separating human cell or a crushing solution thereof, tissue or a crushing solution thereof, serum, preural fluid, ascites fluid, ocular fluid or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with a fluorescence substance, such as fluorescin isothiocyanate (FITC) or the like; and (d) measuring the fluorescence substance with a flow cytometer.

The enzyme-linked immunosorbent assay (ELISA) comprises the steps of: (a) separating human cell or a crushing solution thereof, tissue or a crushing solution thereof, serum, preural fluid, ascites fluid, ocular fluid or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with an enzyme, such as peroxydase, biotin or the like; and (d) measuring the resultant developed dye with an absorption measuring apparatus.

The radioactive material labeled immunoassay (RIA) comprises the steps of: (a) separating human cell or a crushing solution thereof, tissue or a crushing solution thereof, serum, preural fluid, ascites fluid, ocular fluid, or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with radioactive ray; and (d) measuring the radioactive ray with a scintillation counter or the like.

The immunocyte staining and immunotissue staining methods comprise the steps of: (a) separating human cell, tissue or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with a fluorescence substance, such as fluorescin isothiocyanate (FITC) or the like, or an enzyme, such as peroxydase, biotin, or the like; and (d) observing the cell, tissue or the like with a microscope.

Examples of the methods, using the monoclonal antibody of the present invention, for immunologically detecting human VEGF receptor Flt-1 or a cell in which human VEGF receptor Flt-1 is expressed on the surface thereof and for immunologically detecting and determining soluble human VEGF receptor Flt-1 include immunocyte, staining, Western blotting, sandwich ELISA, and the like. These methods are described below.

(1) Immunocyte staining using monoclonal antibody

Firstly, the cells in which human VEGF receptor Flt-1 is expressed on the cell surface are prepared. Suspending cells as such or adherent cells after detachment of the cells using trypsin-EDTA are suspended, for example, in a buffer solution for immunocyte staining use (PBS containing 1% BSA, 0.02% EDTA and 0.05% sodium azide) and dispensed in $1 \times 10^5$ to $2 \times 10^5$ portions. A culture supernatant of the anti-human VEGF receptor Flt-1 monoclonal antibody-producing hybridoma obtained in the above-described step 1-(4), the purified monoclonal antibody obtained in the above-described step 1-(6) or the monoclonal antibody labeled with biotin by a known method (*Enzyme Antibody Method;* published by Gakusai Kikaku 1985) is diluted with the buffer solution for immunocyte staining use or the buffer solution for immunocyte staining use further supplemented with 10% animal serum to a concentration of 0.1 to 50 μg/ml and dispensed in 20 to 500 μl portions to carry out the reaction under cooling for 30 minutes. When the culture supernatant of the anti-human VEGF receptor Flt-1 monoclonal antibody-producing hybridoma obtained in the above-described step 1-(4) or the purified monoclonal antibody obtained in the above-described step 1-(6) is used in the reaction, the cells are washed with the buffer solution for immunocyte staining use and then an anti-mouse immunoglobulin antibody or anti-rat immunoglobulin labeled with fluorescence dye, such as FITC, phycoerythrin, or the like, which is dissolved in the buffer solution for immunocyte staining use to a concentration of about 0.1 to 50 μg/ml, is dispensed in 50 to 500 μl portions to carry out the reaction under cooling for 30 minutes. When the monoclonal antibody labeled with biotin is used in the reaction, streptoavidin is dispensed in 50 to 500 μl portions and then the reaction is carried out under cooling in the dark for 30 minutes. After completion of the reaction, the cells are thoroughly washed with the buffer solution for immunocyte staining use and analyzed by a cell sorter.

(2) Detection of human VEGF receptor Flt-1 by Western blotting

Cell membrane components are prepared from cells in which human VEGF receptor Flt-1 is expressed, such as human VEGF receptor Flt-1-expressing NIH3T3 cells (referred to as "NIH3T3-Flt-1" hereinafter), and from control cells such as NIH3T3 cells (referred to as "NIH3T3-Neo" hereinafter) (*Oncogene,* 10, 135 (1995)), and the membrane components are subjected to electrophoresis by the SDS-PAGE method under reducing conditions in an amount of 0.1 to 30 μl as protein per lane. The thus treated proteins are transferred on a PVDF membrane and allowed to react with PBS containing 1% BSA at room temperature for 30 minutes to effect blocking. They are allowed to react with the culture supernatant of the anti-human VEGF receptor Flt-1 monoclonal antibody-producing hybridoma obtained in the above-described step 1-(4) or the purified monoclonal antibody obtained in the above-described step 1-(6), washed with PBS containing 0.05% Tween and then allowed to react with peroxidase-labeled goat anti-mouse IgG at room temperature for 2 hours. After washing with PBS containing 0.05% Tween, bands to which the anti-human VEGF receptor Flt-1 monoclonal antibody is linked are detected using ECL™ Western blotting detection reagents (produced by Amersham) or the like.

(3) Determination of soluble VEGF receptor Flt-1 using monoclonal antibody

As a first antibody, the purified monoclonal antibody obtained in the above-described step 1-(6) is coated on an appropriate plate and allowed to react with 0.056 to 10,000 ng/ml of the purified soluble anti-human VEGF receptor Flt-1 monoclonal antibody-producing hybridoma obtained in the above-described step 1-(1), or with a sample, such as human serum or the like. After through washing of the plate, this is allowed to react with a second antibody, namely a monoclonal antibody labeled with biotin, an enzyme, a chemiluminescence substance, a radioactive compound or the like, which is one of the purified monoclonal antibodies obtained in the above-described step 1-(6) but recognizes different epitope from that of the monoclonal antibody used as the first antibody, under reaction conditions suitable for binding of the labeled antibody to the epitope with which it binds. A calibration curve is prepared based on the reactivity for the purified soluble VEGF receptor Flt-1, and the concentration of the soluble VEGF receptor Flt-1 in the samples is calculated.

The inhibition methods of the bonding of human VEGF to human VEGF receptor Flt-1 and of the biological activities of human VEGF are exemplified.

(4) Test on the inhibition of the binding of VEGF to VEGF receptor Flt-1 using monoclonal antibody Methanol is dispensed in 100 μl portions into wells of a 96 well MultiScreen-IP Plate (produced by Millipore) to give hydrophilic nature to the PVDF membrane on the bottom of the plate. After washing with water, human VEGF receptor Flt-1 or a recombinant protein such as a fusion protein with human VEGF receptor Flt-1 is diluted to a concentration of 0.1 to 10 μg/ml, dispensed in 50 μl/well portions and then allowed to stand overnight at 4° C. to effect its adsorption. After washing, PBS containing 1% bovine serum albumin (BSA) is dispensed in 100 μl/well portions and the reaction is carried out at room temperature for 1 hour to effect blocking of any remaining active groups. After washing with PBS, the culture supernatant of the anti-human VEGF receptor Flt-1 monoclonal antibody-producing hybridoma obtained in the above-described step 1-(4) or the purified monoclonal antibody obtained in the above-described step 1-(6) is dispensed in 50 μl/well portions and then 0.1 to 10 ng/ml of $^{125}$I-labeled VEGF (produced by Amersham) is dispensed in 50 μl/well portions, subsequently carrying out the reaction at room temperature for 1.5 hours. After washing with 0.05% Tween-PBS, the wells are dried at 50° C., and a scintillator is dispensed in 20 to 100 μl/well portions to measure the radioactivity of the $^{125}$I-labeled VEGF linked to each well using Top Count (produced by Packard) or the like.

(5) Test on the inhibition of the binding of VEGF to VEGF receptor Flt-1 expressing cells using monoclonal antibody PBS containing 1% bovine serum albumin (BSA) is dispensed in 100 μl portions into wells of a 96 well MultiScreen-HV Plate (produced by Millipore), the reaction is carried out at room temperature for 1 hour to effect blocking of the active groups in wells and then NIH3T3-Flt-1 cells suspended in 1% BSA-PBS containing 0.05% NaN$_3$ is dispensed in $1 \times 10^4$ to $1 \times 10^5$/well portions. After washing with 1% BSA-PBS, the culture supernatant of the anti-human VEGF receptor Flt-1 monoclonal antibody-producing hybridoma obtained in the above-described step 1-(4) or the purified monoclonal antibody obtained in the above-described step 1-(6) is dispensed in 50 μg/well portions nd then 0.1 to 10 ng/ml of $^{125}$I-labeled VEGF (produced by Amersham) is dispensed in 50 μl/well portions, subsequently carrying out the reaction at room temperature for 1.5 hours. After washing with PBS, the wells are dried at 50° C., and a scintillator is dispensed in 20 to 100 μl/well portions to measure the radioactivity of the $^{125}$I-labeled VEGF linked to each well using Top Count (produced by Packard) or the like.

The present invention renders possible provision of monoclonal antibodies that specifically binds to human VEGF receptor Flt-1 which is considered to be expressed specifically in vascular endothelial cells of human angiogenesis regions. The monoclonal antibodies of the present invention are useful for the immunological detection of human angiogenesis regions by immunocyte staining and for the diagnosis or treatment, through the inhibition of the biological activities of human VEGF, or diseases in which their morbid states progress by abnormal angiogenesis, such as proliferation or metastasis of solid tumors, arthritis in rheumatoid arthritis, diabetic retinopathy, retinopathy of prematurity, psoriasis, and the like.

EXAMPLE 1

1. Preparation of antigen (1) Construction of soluble human VEGF receptor Flt-1 3N expression vector A vector was prepared in the following manner, for use in the expression of a soluble human VEGF receptor Flt-1 fragment (referred to as "soluble human VEGF receptor Flt-1 3N" hereinafter) which corresponds to a region of the 1st to 338th positions (including a signal sequence) from the N-terminal amino acid of human VEGF receptor Flt-1. The soluble human VEGF receptor Flt-1 3N corresponds to the N-terminal side three immunoglobulin-like regions of the extracellular domain of the soluble human VEGF receptor Flt-1.

A cDNA clone flt#3-7 (M. Shibuya et al., *Oncogene*, 5, 519, 1990) which contains whole length cDNA coding for the human VEGF receptor Flt-1 was partially digested with restriction enzymes EcoRI and TaqI to collect a 1,263 bp EcoRI-TaqI DNA fragment from the 5'-end, and the thus collected fragment was inserted into the 5' side EcoRI site and 3' side NotI site downstream of the transcription initiation point of the polyhedrin gene of a baculovirus gene recombinant vector pVL1393 plasmid (produced by Invitrogen) using a TaqI-NotI adapter into which a termination codon had been artificially introduced (a synthetic DNA fragment having the nucleotide sequences shown in the SEQ ID NO:1 and NO:2), thereby obtaining soluble human VEGF register Flt-1 3N expression vector pVL1393/Flt 3N (FIG. 1).

(2) Construction of soluble human VEGF receptor Flt-1 7N expression vector

A vector was prepared in the following manner, for use in the expression of a soluble human VEGF receptor Flt-1 fragment (referred to as "soluble human VEGF receptor Flt-1 7N" hereinafter) which corresponds to a region of the 1st to 750th positions (including a signal sequence) from the N-terminal amino acid of human VEGF receptor Flt-1. The soluble human VEGF receptor Flt-1 7N corresponds to the seven immunoglobulin-like regions of the extracellular domain of the soluble human VEGF receptor Flt-1.

Figure 2:
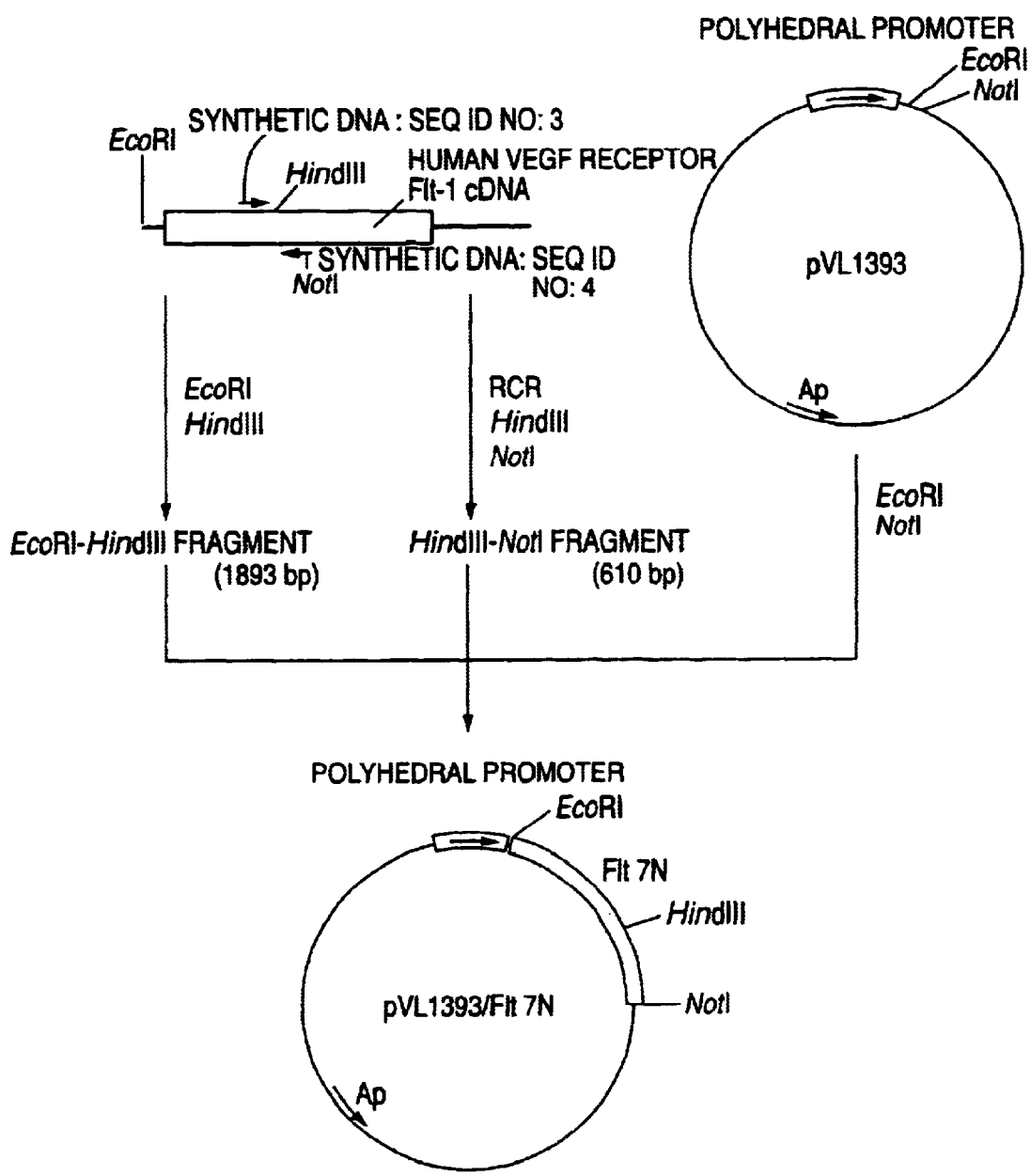
FIG. 2 is a graph showing construction steps of plasmid pVL1393/Flt 7N.

A 2.5 unit portion of the Taq polymerase was added to 100 $\mu$l of 0.001% (w/v) gelatin solution of 10 mM $MgCl_2$ containing 10 pmol of primers having the nucleotide sequences shown in SEQ ID NO:3 and NO:4, 10 ng of flt#3-7clone (*Oncogene*, 5, 519, (1990)) DNA and 10 mM deoxynucleotide triphosphates. The polymerase chain reaction (PCR) was repeated 30 times in which one reaction consisted, after pretreatment of 95° C. for 5 minutes, of treatments at 95° C. for 90 seconds, at 50° C. for 90 seconds and finally at 72° C. for 90 seconds, subsequently collecting a DNA fragment. The DNA fragment was digested with HindIII (the 1893 bp position in the flt#3-7 clone) and NotI to obtain a 610 bp HindIII-NotI DNA fragment, namely a DNA fragment containing a 1894–2499 bp fragment of the flt#3-7 clone, termination codon and NotI recognition sequence. Next, the flt#3-7 clone was digested with restriction enzymes EcoRI and HindIII to collect an EcoRI-HindIII fragment of 1893 bp from the 5'-end. The 610 bp HindIII-NotI DNA fragment and the 1893 bp EcoRI-HindIII fragments were then inserted into the 5' side EcoRI site and 3' side NotI site downstream of the transcription initiation point of the polyhedrin gene of a baculovirus gene recombinant vector pVL1393 plasmid, thereby preparing soluble human VEGF receptor Flt-1 7N expression vector pVL1393/Flt 7N (FIG. 2).

(3) Preparation of recombinant virus for use in the expression of soluble human VEGF receptor Flt-1 in insect cells.

For the production of protein by insect cells, it is necessary to prepare a recombinant virus into which a gene of interest is integrated, and the preparation process consists of a step in which a cDNA molecule coding for a protein of interest is inserted into a special plasmid, which is called a transfer vector, and a subsequent step in which a wild type virus and the transfer vector are co-transfected into insect cells to obtain a recombinant virus by homologous recombination. These steps were carried out in the following manner using BaculoGold Starter Kit manufactured by Pharmingen (product no. PM-21001K) in accordance with the manual.

A recombinant baculovirus was prepared in the following manner by introducing a filamentous baculovirus DNA (BaculoGold baculovirus DNA, produced by Pharmigen) and the thus prepared transfer vector DNA into insect cells Sf9 (produced by Pharmigen) which had been cultured using TMN-FH insect medium (produced by Pharmigen), using a lipofectin method (*Protein, Nucleic Acid, Enzyme*, 37, 2701 (1992)).

A 1 $\mu$g portion of pVL1393/Flt7N prepared in the above step (2) or pVL1393/Flt3N prepared in the above step (1) and 20 ng of filamentous baculovirus DNA were dissolved in 12 $\mu$l of distilled water, the solution was mixed with a mixture of 6 $\mu$l lipofectin and 6 $\mu$l distilled water and then the resulting mixture was allowed to stand at room temperature for 15 minutes. Separately from this, $1\times10^6$ to Sf9 cells were suspended in 2 ml of Sf900-II medium (produced by Gibco) and put into a cell culture plastic Petri dish of 35 mm in diameter. To this was added whole volume of the just described solution of plasmid DNA, filamentous baculovirus DNA and lipofectin mixture, followed by 3 days of culturing at 27° C. to collect 1 ml of the culture supernatant containing the recombinant virus. A 1 ml portion of Sf900-II medium was added to the resulting Petri dish and 3 days of culturing was carried out at 27° C. to obtain an additional 1.5 ml of the recombinant virus containing culture supernatant.

Next, the thus obtained recombinant virus for use in the protein expression was grown in the following manner.

A $2\times10^7$ portion of Sf9 cells were suspended in 10 ml of Sf900-II medium, put into a 175 $cm^2$ flask (produced by Greiner) and allowed to stand at room temperature for 1 hour to effect adhesion of the cells to the flask. The supernatant fluid was subsequently discarded and 15 ml of fresh TMN-FH insect medium and a 1 ml portion of the recombinant virus containing culture supernatant described above were added and cultured for 3 days at 27° C. After the culturing, the supernatant fluid was centrifuged at 1,500× g for 10 minutes to remove the cells, thereby obtaining a recombinant virus solution for use in the protein expression.

The titer of virus in the thus obtained recombinant virus solution was calculated by the method described in BaculoGold Starter Kit Manual (Pharmigen).

A $6\times10^6$ portion of Sf9 cells were suspended in 4 ml of Sf900-II medium, put into a cell culture plastic Petri dishes at 60 mm in diameter and allowed to stand at room temperature for 1 hour to effect adhesion of the cells to the dish. Next, the supernatant fluid was discarded, 400 μl of fresh Sf900-II medium and the above-described recombinant virus solution diluted 10,000 times with Sf900-II medium were adapted to the dish and allowed to stand at room temperature for 1 hour, the medium was removed and then 5 ml of a medium containing 1% low melting point agarose (Agarplaque Agarose, produced by Pharmigen) (prepared by mixing 1 ml of sterilised 5% Agarplaque plus agarose aqueous solution with 4 ml of TMN-FH insect medium and stored at 42° C.) was poured into the dish. After standing at room temperature for 15 minutes, the dish was tied with a vinyl tape to prevent drying, put into a sealable plastic container and then subjected to 6 days of culturing at 27° C. A 1 ml portion of PBS containing 0.01% of Neutral Red was added to the dish to carry out the additional culturing for 1 day and then the number of the thus formed plaques was counted. By the above procedure, it was found that each of the recombinant virus solutions contained virus particles of about $1 \times 10^7$ plaque forming units (referred to as "PFU" hereinafter) per ml.

(4) Expression of soluble human VEGF receptors Flt-1 7N and Flt-1 3N in insect cells and purification thereof Soluble human VEGF receptors Flt-1 7N and Flt-1 3N were obtained in the following manner. A $4 \times 10^7$ portion of High Five cells were suspended in 30 ml of EX-CELL™ 400 medium (produced by JRH Biosciences) contained in a 175 cm² flask (produced by Greiner) and allowed to stand at room temperature for 1 hour to effect adhesion of the cells to the flask. A 1 ml portion of a solution containing about 1 to $3 \times 10^8$ PFU/ml or recombinant virus particles obtained in the above step (3) from the transfer vectors pVL1393/Flt 7N and pVL1393/Flt 3N was added to the flask to carry out infection at room temperature for 2 hours. The culture supernatant was removed and 30 ml of fresh EX-CELL™ 400 medium was added to carry out 3 to 4 days of culturing at 27° C. After completion of the culturing, the culture supernatant was collected and centrifuged at 1,500× g for 10 minutes to obtain a supernatant fluid.

A column was packed with about 60 ml of heparin-Sepharose CL-6B cell gel (produced by Pharmacia Biotech AB) and washed with 600 ml of 20 mM Tris-HCl (pH 7.5) buffer at a flow rate of 0.5 ml/minute. After the washing, 1,000 ml of the culture medium containing soluble human VEGF receptors Flt-1 7N and Flt-1 3N, which had been prepared in the above-described manner, was passed through the haparin-Sepharose CL-6B column at a flow rate of 0.5 ml/minute. After washing with 600 ml of 20 mM Tris-HCl (pH 7.5) buffer at a flow rate of 0.5 ml/minute, 600 ml of 20 mM Tris-HCl (pH 7.5) buffer having a density gradient of 0 M to 1.1 M NaCl was passed through the column to carry out elution of the proteins adsorbed to the heparin-Sepharose, and the eluate was fractionated in 8 ml portions. Proteins contained in each fraction were anlaysed by SDS polyacrylamide gel electrophoresis (SDS-PAGE), and 60 to 80 ml of fractions containing soluble human VEGF receptors Flt-1 7N and Flt-1 3N were collected and concentrated using CentriPrep 10 (produced by Amicon). After the concentration, soluble human Flt-1 7N and Flt-1 3N were obtained as solutions of 5 ml and 13 ml, respectively (protein concentrations were 331 μg/ml and 204 μg/ml).

Figure 3:
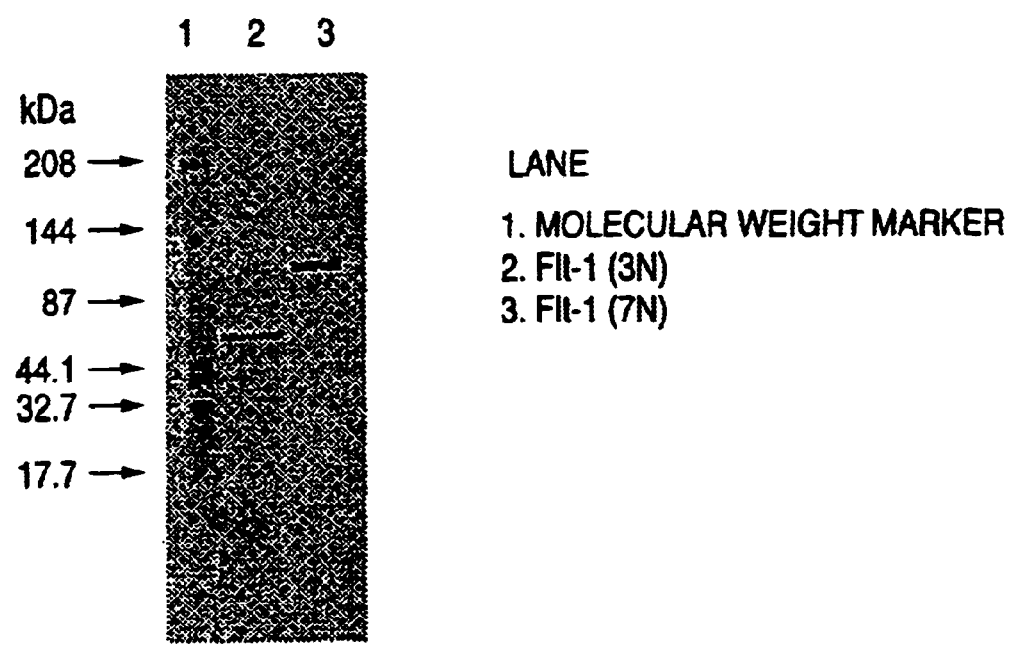
FIG. 3 is a graph showing patterns of SDS polyacrylamide electrophoresis (a 5 to 20% gradient gel was used) of purified Flt-1 7N and Flt-1 3N. Starting from the left side, electrophoresis patterns of molecular weight markers, Flt-1 3N and Flt-1 7N are shown respectively. The electrophoresis was carried out under reducing conditions.

(5) Confirmation of the purity of soluble human VEGF receptors Flt-1 7N and Flt-1 3N Purity of the thus purified soluble human VEGF receptors Flt-1 7N and Flt-1 3N was confirmed by SDS-PAGE. The SDS-PAGE was carried out in accordance with a known method (*Anticancer Research*, 12, 1121, 1992). Using a 5 to 20% gradient gel (produced by Atto) as the gel, electrophoresis of Flt-1 7N and Flt-1 3N, each 2 μg as protein per lane, was carried out under reducing conditions, and the resulting gel was stained with Coomassie Billiant Blue. The results are shown in FIG. 3. Purity of Flt-1 7N and Flt-1 3N was found to be 95% or more.

(6) Purification of control antigen protein of soluble human VEGF receptors Flt-1 7N and Flt-1 3N The control antigen protein (negative control protein) of soluble human VEGF receptors Flt-1 7N and Flt-1 3N was obtained in the following manner. A $4 \times 10^7$ portion of High Five cells were suspended in 30 ml of EX-CELL™ 400 medium (produced by JRH Biosciences) contained in a 175 cm² flask (produced by Greiner), allowed to stand at room temperature for 1 hour to effect adhesion of the cells to the flask and then cultured at 27° C. for 3 to 4 days. After completion of the culturing, the culture supernatant was collected and centrifuged at 1,500× g for 10 minutes to obtain a supernatant fluid.

A column was packed with about 20 ml of heparin-Sepharose CL-6B gel (produced by Pharmacia Biotech AB) and washed with 200 ml of 20 mM Tris-HCl (pH 7.5) buffer at a flow rate of 0.5 ml/minute. After the washing, 500 ml of the culture medium of High Five cells was passed through the heparin-Sepharose CL-6B column at a flow rate of 0.5 ml/minute. After washing with 200 ml of 20 mM Tris-HCl (pH 7.5) buffer at a flow rate of 0.5 ml/minute, 200 ml of 20 mM Tris-HCl (pH 7.5) buffer containing 1 M NaCl was passed through the column to carry out elution of the protein adsorbed to the heparin-Sepharose. The 1 M NaCl elution fraction was concentrated using CentriPrep 10 (produced by Amicon) to obtain 7 ml of the control antigen protein (867 μg/ml as protein concentration).

(7) Concentration of human VEGF binding activity of soluble human VEGF receptors Flt-1 7N and Flt-1 3N The human VEGF binding activity of soluble human VEGF receptors Flt-1 7N and Flt-1 3N was confirmed in the following manner.

Methanol was dispensed in 100 μl portions into wells of a 96 well Immobilon™-P Filtration Plate (produced by Millipore) to give a hydrophilic nature to the PVDF membrane on the bottom of the plate. After washing with water, the soluble human Flt-1 7N diluted to a concentration of 2 μg/ml was dispensed in 50 μl/well portions and allowed to stand overnight at 4° C. to effect its adsorption. After washing, PBS containing 1% bovine serum albumin (BSA) was dispensed in 100 μl/well portions and 1 hour of the reaction was carried out at room temperature to effect blocking of the remained active groups. After washing with PBS, each of the purified soluble human VEGF receptors Flt-1 7N and Flt-1 3N obtained in the above-described step (4) was dispensed in 50 μl/well portions (final concentration, 1 to 1,000 ng/ml) and then $^{125}$I-labeled human VEGF (final concentration, 3 ng/ml: produced by Amersham) was dispensed in 50 μl/well portions, subsequently carrying out the reaction at room temperature for 1.5 hours. After washing with 0.05% Tween-PBS, the wells were dried at 50° C., and Microscinti-0 (produced by Packard) was dispensed in 20 μl/well portions to measure the radioactivity of the $^{125}$I-labeled human VEGF linked to each well using Top Count (produced by Packard).

Figure 4:
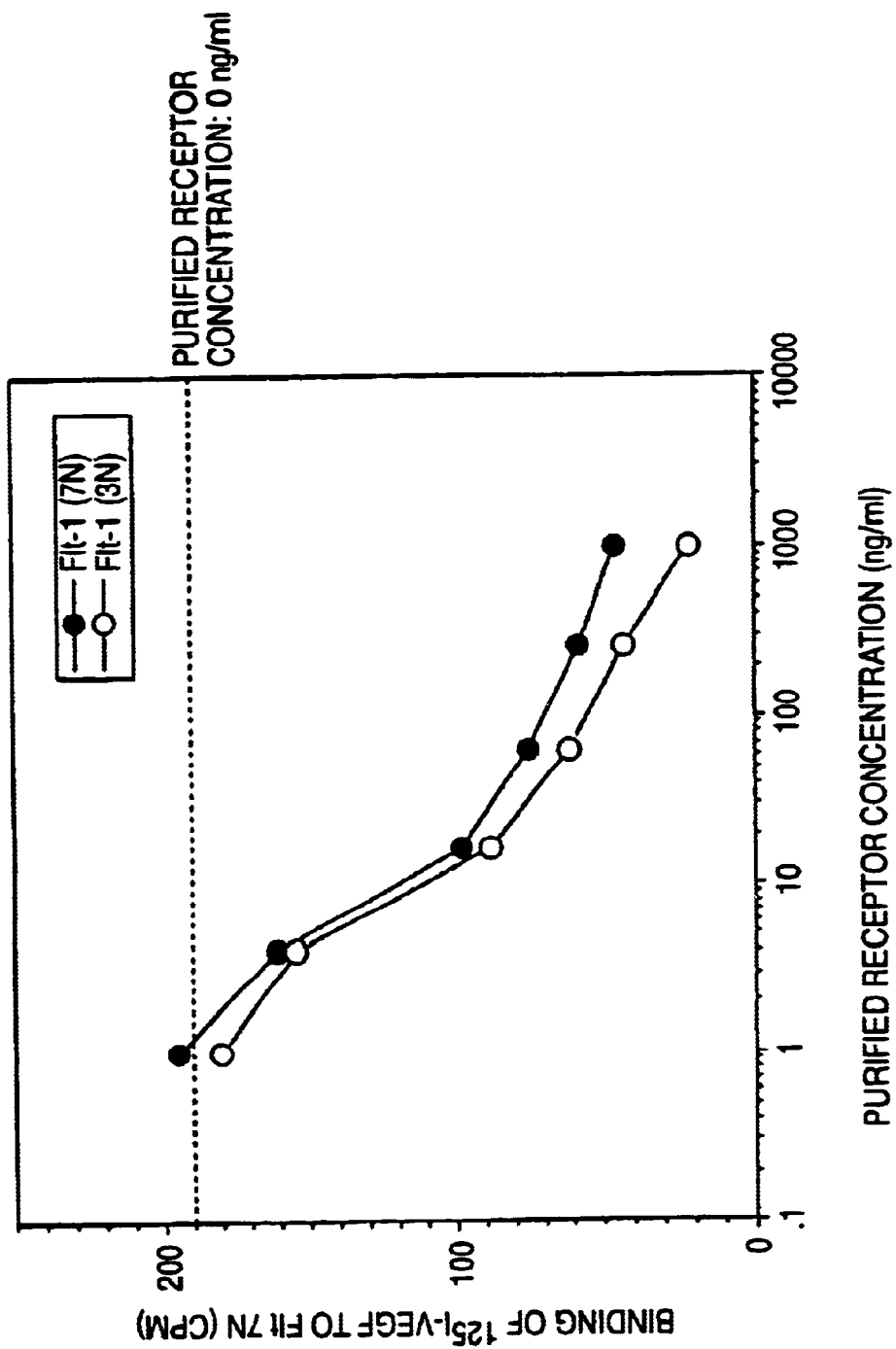
FIG. 4 is a graph showing results of the analysis of the effect of soluble human VEGF receptors Flt-1 7N and Flt-1 3N to inhibit binding of a $^{125}$I-human VEGF to a plate-coated soluble human VEGF receptor Flt-1 7N.

The results are shown in FIG. 4. It was shown that soluble human VEGF receptors Flt-1 7N and Flt-1 3N inhibit binding of $^{125}$I-labeled human VEGF to soluble human VEGF receptor Flt-1 7N in a concentration dependent manner. Since the soluble human VEGF receptors Flt-1 7N and Flt-1 3N showed similar degrees of the human VEGF binding activity, it was revealed that the human VEGF binds to the Flt-1 3N moiety (the 1st to 338th positions from the N-terminal amino acid including signal sequence).

(8) Expression of human VEGF in insect cells

The human VEGF was obtained in the following manner. A $4 \times 10^7$ portion of High Five cells were suspended in 30 ml of EX-CELL™ 400 medium (produced by JRH Biosciences) contained in a 175 cm² flask (produced by Greiner) and allowed to stand at room temperature for 1 hour effect adhesion of the cells to the flask. A 1 ml portion of a solution containing about 1 to $3 \times 10^8$ PFU/ml of human VEGF recombinant baculovirus particles obtained in accordance with the known method (*Cell Growth & Differentiation*, 7, 213 (1996)) was added to the flask to carry out infection at room temperature for 2 hours. The culture supernatant was removed and 30 ml of fresh EX-CELL™ 400 medium was added to carry out 3 to 4 days of culturing at 27° C. After completion of the culturing, the culture supernatant was collected and centrifuged at 1,500× g for 10 minutes to obtain a supernatant fluid.

A column was packed with about 40 ml of heparin-Sepharose CL-6B gel (produced by Pharmacia Biotech AB) and washed with 400 ml of 20 mM Tris-HCl (pH 7.5) buffer at a flow rate of 0.5 ml/minute. After washing, 1,500 ml of the culture medium containing human VEGF prepared in the above-described manner was passed through the heparin-Sepharose CL-6B column at a flow rate of 0.5 ml/minute. After washing with 400 ml of 20 mM Tris-HCl (pH 7.5) buffer at a flow rate of 0.5 ml/minute, 120 ml of each of 20 mM Tris-HCl (pH 7.5) buffers containing 0.2 M, 0.5 M and 1 M NaCl was passed through the column in that order to carry out stepwise elution of the proteins adsorbed to the heparin-Sepharose, and the eluate was fractionated in 8 ml portions. Proteins contained in each fraction were analyzed by SDS polyacrylamide gel electrophoresis, and 120 ml of fractions (0.5 to 1 M NaCl fractions) containing human VEGF were collected. After concentration using CentriPrep-10 (produced by Amicon), human VEGF was obtained as 4 ml of solution (protein concentration, 1.2 mg/ml).

2. Immunization of animals and preparation of antibody producing cells

A 50 µg portion of each of the antigens obtained in the above-described step 1-(4) was administered, together with 2 mg of aluminum hydroxide gel and $1 \times 10^9$ cells of pertussis vaccine (produced by Chiba Serum Institute), into 5-week-old female BALB/c mice (SLC Japan), B6C3F1 mice (Charles River Japan) or female SD rates (SLC Japan), and, starting on 2 weeks thereafter, 10 to 50 µg of the protein was administered once a week for a total of four times. Also, $1 \times 10^7$ of NIH3T3-Flt-1 cells were administered 6 times into three, 5 week old female BALB/c (SLC Japan) mice. Blood samples were collected from the fundus of the eye or the caudal vein, their serum antibody titers were examined by the enzyme immunoassay described in the following, and spleens were excised from mice or rats showing sufficient antibody titer 3 days after the final immunization. In this connection, immunization was not induced in the 5-week-old female BALB/c to which NIH3T3-Flt-1 cells were administered, so that the antibody titer upon soluble FLt-1 7N was not increased.

The thus excised spleen was cut to pieces in MEM medium (produced by Nissui Pharmaceutical), unbound using a pair of forceps and then centrifuged (1,200 rpm for 5 minutes). The resulting supernatant was discarded, and the thus obtained sediment was treated with Tris-ammonium chloride buffer (pH 7.65) for 1 to 2 minutes to eliminate erythrocytes, washed three times with MEM medium and used in cell fusion.

3. Enzyme immunoassay

With regard to the measurement of antisera derived from mice or rats immunized with the soluble human Flt-1 7N and Flt-1 3N obtained in the above-described step 1-(4) and culture supernatants of hybridomas, the soluble human VEGF receptors Flt-1 7N and Flt-1 3N obtained from the insect cell culture supernatant of 1-(4) were used as antigens. A 1 to 10 µg/ml PBS-diluted solution of each of the soluble human VEGF receptors Flt-1 7N and Flt-1 3N and the heparin column adsorption fraction of High Five cell culture supernatant obtained in the above-described step 1-(6) as a control antigen was dispensed in 50 µl/well portions into a 96 well plate for EIA (produced by Greiner) and allowed to stand overnight at 4° C. for coating. After washing, PBS containing 1% bovine serum albumin (BSA) was dispensed in 100 µl/well portions and 1 hour of the reaction was carried out at room temperature to effect blocking of the remained active groups. After discarding 1% BSA-PBS, antiserum of immunized mouse or immunized rat and culture supernatant of a hybridoma were dispensed in 50 µl/well portions to carry out the reaction for 2 hours. After washing with 0.05% Tween-PBS, peroxidase-labeled rabbit anti-mouse immunoglobulin or peroxidase-labeled rabbit anti-rat immunoglobulin (both produced by DAKO) was dispensed in 50 µl/well portions and 1 hour of the reaction was carried out at room temperature, the plate was washed with 0.05% Tween-PBS and then color development was caused using ABTS substrate solution (2,2-azinobis(3-ethylbenzothiazole-6-sulfonic acid) ammonium salt) to measure maximum absorbance at OD415 nm using E max (produced by Molecular Devices).

4. Preparation of mouse mycloma cells

8-Azaguanine-resistant mouse myeloma cell line P3U1 was cultured using normal medium to secure $2 \times 10^7$ or more of the cells for use in cell fusion as the parent cell line.

5. Preparation of hybridoma

The mouse spleen cells or rat spleen cells obtained in the above-described section 2 and the myeloma cells obtained in the above section 4 were mixed to a ratio of 10:1 and centrifuged (1,200 rpm for 5 minutes), the supernatant was discarded, the precipitated cells were thoroughly loosened to which, while stirring at 37° C., were subsequently added a mixed solution of 2 g polyethylene glycol-1000 (PEG-1000), 2 ml MEM medium and 0.7 ml DMSO in an amount of 0.2 to 1 ml/$10^8$ mouse myeloma cells and then 1 to 2 ml of MEM medium several times at 1 to 2 minute intervals, and then the total volume was adjusted to 50 ml by adding MEM medium. After centrifugation (900 rpm for 5 minutes), the supernatant was discarded and the thus obtained cells were gently loosened and then gently suspended in 100 ml of HAT medium by repeated drawing up into and discharging from a graduated pipette.

The suspension was dispensed in 100 µl portions into wells of a 96 well culture plate and cultured at 37° C. for 10 to 14 days in an atmosphere of 5% $CO_2$ in a 5% $CO_2$ incubator. The resulting culture supernatant was examined by the enzyme immunoassay method described in Example 1–3 to select wells which reacted specifically with the soluble human VEGF receptor Flt-1 7N or Flt-1 3N obtained in the above-described step 1-(4) but did not react with the control antigen obtained in the step 1-(6), and then cloning was repeated twice by changing the medium to HT medium and normal medium to establish hybridomas capable of producing anti-human VEGF receptor Flt-1 monoclonal antibodies. The results are shown in the following table.

TABLE 1

| Animal | Head | Immuno-gen | Screen-ing source | Wells screened | The number of hybridomas established |
|---|---|---|---|---|---|
| Balb/c mouse | 3 | NIH3T3-Flt-1 | Flt 7N | — | — |
| SD rat | 1 | Flt 7N | Flt 7N | 1008 | 3 (KM1733,1735,1736) |
| Balb/c mouse | 1 | Flt 7N | Flt 7N | 672 | 5 (KM1737,1739,1740) 1742,1743) |
| SD rat | 1 | Flt 7N | Flt 7N | 1176 | 3 (KM1745,1746,1747) |
| B3C3F1 mouse | 1 | Flt 7N | Flt 3N | 672 | 3 (KM1748,1749,1750) |
| Balb/c mouse | 1 | Flt 7N | Flt 3N | 420 | 3 (KM1730,1731,1732) |

When hybridomas obtained from one Balb/c mouse and two SD rate immunized with the soluble human VEGF receptor Flt-1 7N prepared in the above-described step 1-(4) were screened for about 672 wells and about 2,184 wells, respectively, using the soluble human VEGF receptor Flt-1 7N, respective 5 clones and 6 clones of anti-human VEGF receptor Flt-1 monoclonal antibodies were obtained, and they were named KM1737, KM1739, KM1740, KM1742 and KM1743 and KM1733, KM1735, KM1736, KM1745, KM1746 and KM1747, respectively. None of these clones showed the action to inhibit binding of human VEGF to Flt-1 as shown in the following section 8. Additionally, KM1735, KM1736, KM1742, KM1743 and KM1745 reacted with human VEGF receptor Flt-1 expression cells by the immunocyte staining method described in the following section 10, but the reaction was extremely weak in comparison with KM1730, KM1731 and KM1732.

On the other hand, when hybridomas obtained from one B3C3F1 mouse and one Balb/c mouse immunized with the soluble human VEGF receptor Flt-1 7N prepared in the above-described step 1-(4) were screened for about 672 wells and about 420 wells, respectively, using the soluble human VEGF receptor Flt-1 3N, 3 clones for each of anti-human VEGF receptor Flt-1 monoclonal antibodies were obtained, and they were named KM1748, KM1749 and KM1750 and KM1730, KM1731 and KM1732, respectively. Of these clones, three clones KM1732, KM1748 and KM1750 showed the action to inhibit binding of human VEGF to Flt-1 as shown in the following section 8. Additionally, three clones KM1730, KM1731 and KM1732 reacted markedly strongly with human VEGF receptor Flt-1 expression cells by the immunocyte staining method described in the following section 10.

The antibody class of these monoclonal antibodies was determined by enzyme immunoassay using Subclass Typing Kit (produced by Zymed). The results are shown in the following table.

TABLE 2

| Monoclonal antibody | Antibody subclass |
|---|---|
| KM1733 | mouse IgG2a |
| KM1735 | rat IgG1 |
| KM1736 | rat IgG2a |
| KM1737 | mouse IgG1 |
| KM1739 | mouse IgG1 |
| KM1740 | mouse IgG1 |
| KM1742 | mouse IgG1 |
| KM1743 | mouse IgG1 |
| KM1745 | rat IgG2a |
| KM1746 | rat IgG1 |
| KM1747 | rat IgG1 |
| KM1748 | mouse IgG2b |
| KM1749 | mouse IgG1 |
| KM1750 | mouse IgG2b |
| KM1730 | mouse IgG1 |
| KM1731 | mouse IgG2a |
| KM1732 | mouse IgG1 |

All of the monoclonal antibodies established in the present invention were IgG class.

6. Purification of monoclonal antibody

The hybridomas obtained in the above section 5 were respectively administered to pristane-treated female nude mice (Balb/c) of 8 weeks of age by intraperitoneal injection at a dose of 5 to 20×10$^6$ cells per animal. The hybridomas caused ascites tumor formation in 10 to 21 days. The ascitic fluid was collected from each ascitic fluid-carrying mouse (1 to 8 ml per animal), centrifuged (3,000 rpm for 5 minutes) for removing solid matter and then purified by a caprylic acid precipitation method (Antibodies—A Laboratory Manual).

7. Confirmation of the specificity of monoclonal antibodies

Specificity of the anti-human VEGF receptor Flt-1 monoclonal antibodies described in the above-described section 5 was confirmed using the enzyme immunoassay method described in the above-described section 3.

Figure 5:
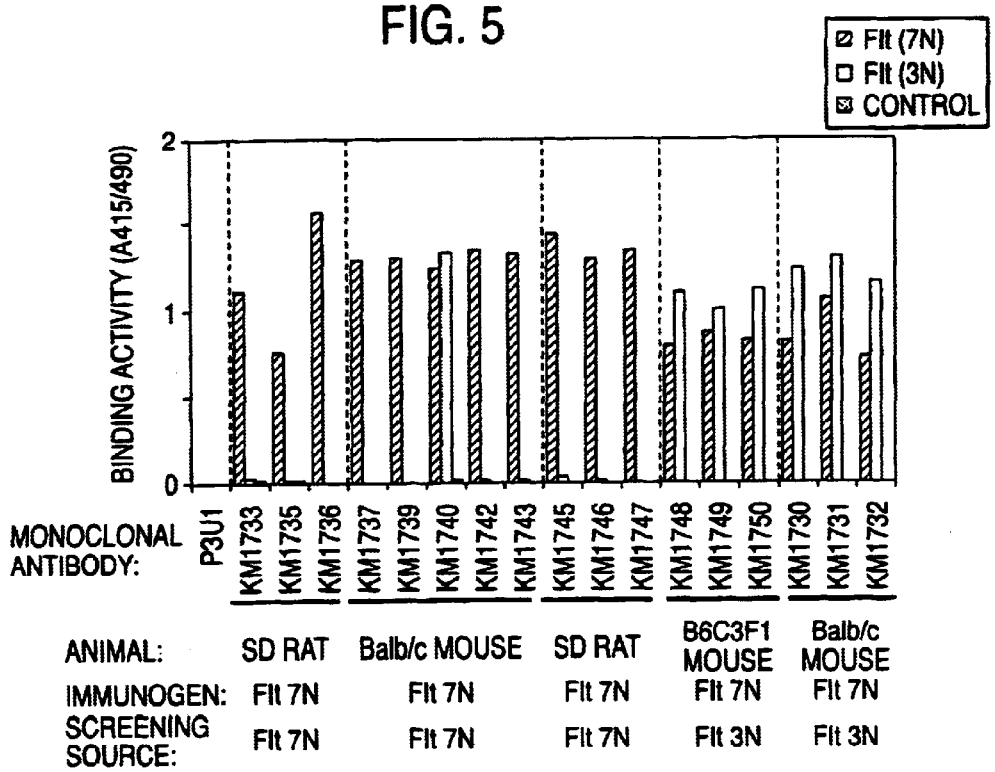
FIG. 5 is a graph showing results of the examination of the binding reactivity of anti-human VEGF receptor Flt-1 monoclonal antibody by enzyme immunoassay.

The results are shown in FIG. 5. Among the monoclonal antibodies obtained by preparing hybridomas from mice and rats immunized with Flt-1 7N and selected using Flt-1 7N (KM1733, KM1735, KM1736, KM1737, KM1739, KM1740, KM1742, KM1743, KM1745, KM1746 and Km1747), only KM1740 reacted with Flt-1 7N and Flt-1 3N, revealing that it recognizes an epitope which is present in a region of the 1st to 338th positions from the N-terminal amino acid of Flt-1 (including signal sequence). Since the remaining 10 clones reacted with Flt-1 7N but not with Flt-1 3N, it was revealed that they recognize an epitope which is present in a region of the 339th to 750th positions from the N-terminal amino acid of Flt-1 (including signal sequence). On the other hand, since all of the monoclonal antibodies obtained by preparing hybridomas from mice immunized with Flt-1 7N and selecting using Flt-1 3N (KM1748, KM1749, KM1750, KM1730, KM1731 and KM1732) reacted with Flt-1 7N and Flt-1 3N, it was revealed that they recognize an epitope which is present in a region of the 1st to 338th positions from the N-terminal amino acid of Flt-1 (including signal sequence).

8. Confirmation of the activity of anti-Flt-1 monoclonal antibodies to inhibit binding of a human VEGF to a human VEGF receptor Flt-1.

The activity of the anti-human VEGF receptor Flt-1 monoclonal antibodies described in the above-described section 5 to inhibit binding of human VEGF to human VEGF receptor Flt-1 was confirmed in the following manner.

Methanol was dispensed in 100 µl portions into wells of a 96 well Multi-Screen-IP Plate (produced by Millipore) to give hydrophilic nature to the PVDF membrane on the bottom of the plate. After washing with water, the soluble human VEGF receptor Flt-1 7N diluted with PBS to a concentration of 1.6 µg/ml was dispensed in 50 µl/well portions and then allowed to stand overnight at 4° C. to effect its adsorption. After washing, PBS containing 1% bovine serum albumin (BSA) is dispensed in 50 μl/well portions and 1 hour of the reaction was carried out at room temperature to effect blocking of the remained active groups. After washing with PBS, each hybridoma culture supernatant or a purified monoclonal antibody diluted with 1% BSA-PBS containing 0.5M NaCl (0.01 to 7.29 μg/ml) was dispensed in 50 μl/well portions and then 3 ng/ml of $^{125}$I-labeled human VEGF (produced by Amersham) was dispensed in 50 μl/well portions, subsequently carrying out the reaction at room temperature for 1.5 hours. After washing with 0.05% Tween-PBS, the wells were dried at 50° C., and Microscinti-0 (produced by Packard) was dispensed in 30 μl/well portions to measure the radioactivity of the $^{125}$I-labeled human VEGF linked to each well using Top Count (produced by Packard).

Figure 6:
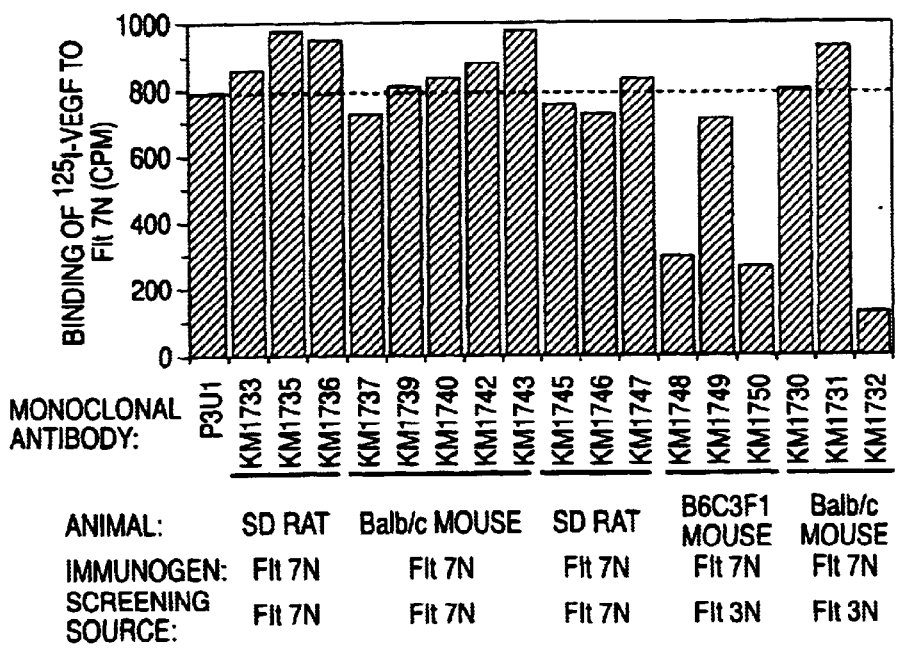
FIG. 6 is a graph showing results of the examination of the activity of anti-human VEGF receptor Flt-1 monoclonal antibody to inhibit binding of VEGF to human VEGF receptor Flt-1.

Results of the examination of activities of hybrimdoma culture supernatants are shown in FIG. 6. Among 17 established monoclonal antibodies, three monoclonal antibodies, KM1748, KM1740 and KM1732 inhibited binding of human VEGF to human VEGF receptor Flt-1 at inhibition ratios of 62.6%, 66.3% and 83.1%, respectively.

In general, screening of monoclonal antibody producing hybridomas is carried out using the same protein as the antigen used as the immunogen. A total of 11 monoclonal antibodies selected using Flt-1 7N as the immunogen showed no binding inhibition activity, and, among 6 monoclonal antibodies selected using Flt-1 3N (KM1748, KMI1749, KM1750, KM1730, KM1731 and KM1732), (KM1748, KM1750 and KM1732 showed the binding inhibition activity. It was an unexpected effect that monoclonal antibodies having the binding inhibition activity were obtained by the use of Flt-1 3N in the screening of hybridomas. Thus, it was revealed that Flt-1 3N is markedly important in establishing monoclonal antibodies having the binding inhibition activity.

Figure 7:
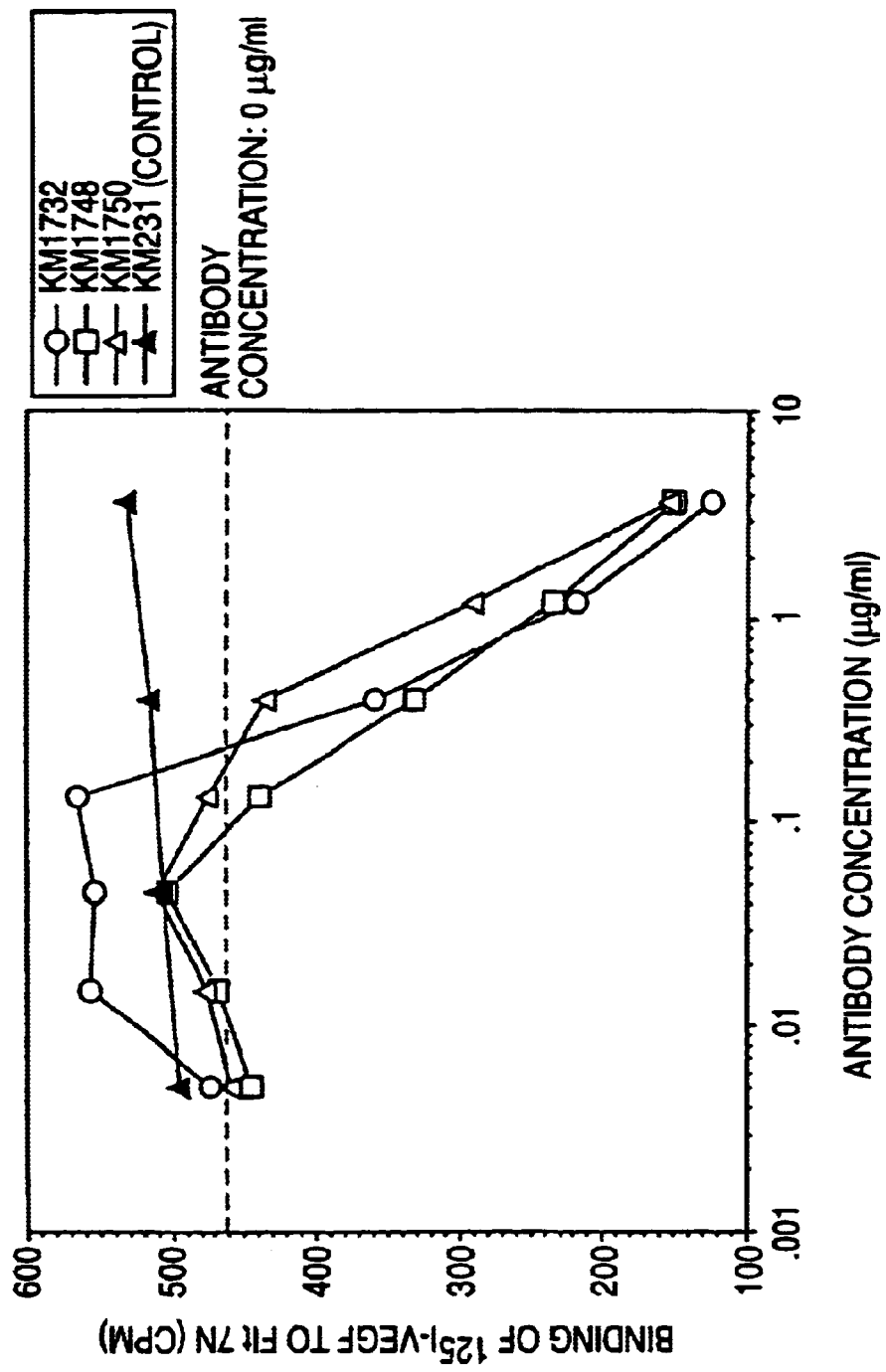
FIG. 7 is a graph showing results of the examination of the activity of anti-human VEGF receptor Flt-1 monoclonal antibodies KM1732, KM1748 and KM1750 to inhibit binding of human VEGF to human VEGF receptor Flt-1.

FIG. 7 shows results of the examination of binding inhibition activity using purified anti-Flt-1 monoclonal antibodies KM1732, Km1748 and KM1750. These antibodies KM1732, KM1748 and KM1750 inhibited binding of human VEGF to human VEGF receptor Flt-1 in a concentration dependent manner. Concentrations of KM1732, KM1748 and KM1750, which indicate 50% inhibition of the binding of human VEGF to human VEGF receptor Flt-1 ($IC_{50}$), were 1.1, 1.3 and 2.0 μg/ml, respectively. On the other hand, an anti-sialyl-Le$^a$ monoclonal antibody KM231 of a mouse IgG1 class (*Anticancer Research*, 10, 1579 (1990)) used as the control showed no inhibition activity.

9. Confirmation of the activity of anti-Flt-1 monoclonal antibodies to inhibit binding of human VEGF to human VEGF receptor Flt-1 expression cells.

The activity of the anti-human VEGF receptor Flt-1 monoclonal antibodies KM1732, KM1748 and KM1750 to inhibit binding of human VEGF to human VEGF receptor FLT-1 was confirmed in the following manner.

PBS containing 1% bovine serum albumin (BSA) was dispensed in 100 μl portions into wells of a 96 well MultiScreen-HV Plate (produced by MILLIPORE), 1 hour of the reaction was carried out at room temperature to effect blocking of the active groups in the wells and then NIN3T3-Flt-1 cells suspended in 1% BSA-PBS containing 0.05% $NaN_3$ were dispensed in $5 \times 10^4$ cells/ well portions. After washing with 1% BSA-PBS, a purified monoclonal antibody (0.01 to 7.29 μg/ml) was dispensed in 50 μl/well portions and then 3 ng/ml of $^{125}$I-labeled human VEGF (produced by Amersham) was dispensed in 50 μl/well portions and the reaction was carried out under cooling for 2 hours. After washing with PBS, the wells were dried at 50° C., and Microscinti-0 (produced by Packard) was dispensed in 30 μl/well portions to measure the radioactivity of the $^{125}$I-labeled human VEGF linked to each well using Top count (produced by Packard).

Figure 8:
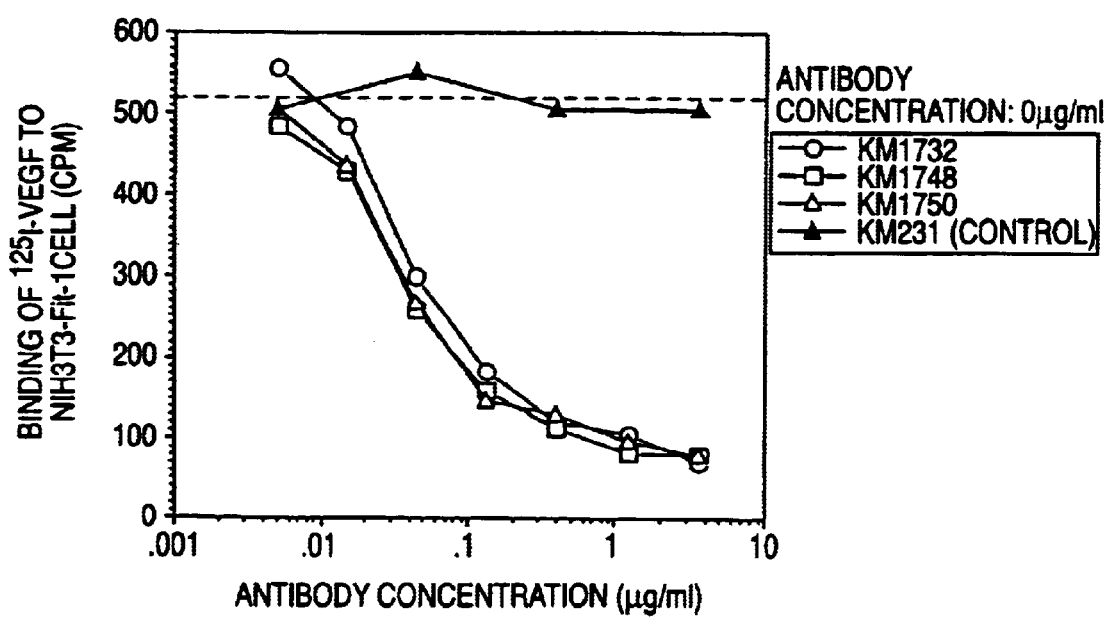
FIG. 8 is a graph showing results of the examination of the activity of anti-human VEGF receptor Flt-1 monoclonal antibodies KM1732, KM1748 and KM1750 to inhibit binding of human VEGF to human VEGF receptor Flt-1 expressing cells.

FIG. 8 shows results of the examination of binding inhibition activity using purified anti-Flt-1 monoclonal antibodies KM1732, KM1748 and KM1750. These antibodies KM1732, KM1748 and KM1750 inhibited binding of human VEGF to NIH3T3-Flt-1 cells in a concentration dependent manner. Concentrations of KM1732, KM1748 and KM1750, which indicate 50% inhibition of the binding of human VEGF to NIH3T3-FLt-1 cells ($IC_{50}$), were 0.050, 0.037 and 0.041 μg/ml, respectively. On the other hand, the anti-sialyl-Le$^a$ monoclonal antibody KM231 of a mouse IgG1 class used as the control showed no inhibition activity.

10. Confirmation of the reactivity of monoclonal antibodies with human VEGF receptor Flt-1 expression cells Specificity of the anti-human VEGF receptor Flt-1 monoclonal antibodies described in the above-described section 5 was confirmed using immunocyte staining method in accordance the following procedure.

A total of $5 \times 10^5$ cells of each of human VEGF receptor Flt-1 expression NIH3T3 cells (NIH3T3-FLT-1) and control NIH3T3 cells (NIH3T3-Neo) (Oncogene, 10, 135 (1995)) were suspended in 100 μl of a buffer solution for immunocyte staining use (PBS containing 1% BSA, 0.02% EDTA and 0.05% sodium azide) and dispensed in a round bottom 96 well plate. After centrifugation at 4° C. and at 350×g for 1 minute, the supernatant fluid was discarded and the resulting cells were mixed with 50 μl of a hybridoma culture supernatant or purified antibody (10 μg/ml) and reaction was carried out at 4° C. for 30 minutes. After the reaction, 200 μl of the buffer solution for immunocyte staining use was added to each well, and the cells were washed by centrifugation at 4° C. and 350×g for 1 minute followed by discarding the resulting supernatant. After repeating this washing step twice, the cells were mixed with 50 μl of the buffer solution for immunocyte staining use containing 1 μg/ml of an FITC-labeled anti-mouse immunoglobulin antibody or FITC-labeled anti-rate immunoglobulin antibody (produced by Wako Pure Chemical Industries), and the reaction was carried out at 4° C. for 30 minutes. After this reaction, the above-described washing step was repeated three times and then analysis was carried out using Flow Cytometer (produced by Coulter).

Figure 9:
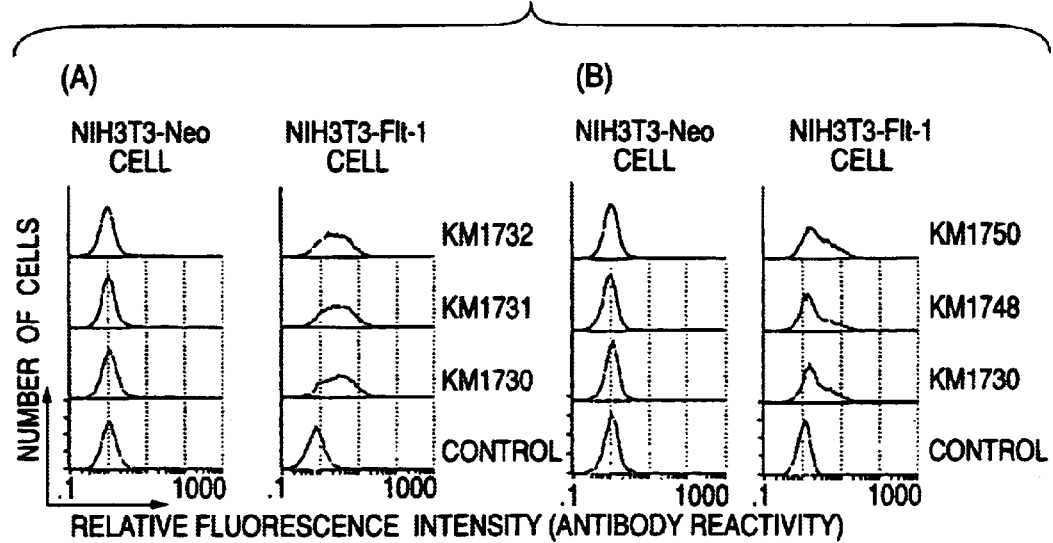
FIG. 9 is a graph showing results of the flow cytometry analysis of the reactivity of anti-human VEGF receptor Flt-1 monoclonal antibodies KM1730, KM1731, KM1732, KM1748 and KM1750 with human VEGF receptor Flt-1-expressing cells NIH3T3-Flt-1 and control cells NIH3T3-Neo cells.

The results are shown in FIG. 9. The anti-human VEGF receptor Flt-1 monoclonal antibodies KM1730, KM1731 and KM1732 did not react with the control cells but specifically reacted in significant amounts with the Flt-1 expression cells. Neither, the anti-human VEGF receptor Flt-1 monoclonal antibody KM1748 (10 μg/ml) nor the hybridoma culture supernatant KM1748 reacted with the control cells. Each specifically reacted in significant amounts with the Flt-1 expression cells (B). As the results, it was discovered that the monoclonal antibodies KM1730, KM1731, KM1732, KM1748 and KM1750 specifically recognize the human VEGF receptor Flt-1 on the cell surface. On the other hand, KM1735, KM1736, KM1742, KM1743 and KM1745 only weakly reacted with the human VEGF receptor Flt-1 expression cells in comparison with KM1730, KM1731, KM1732, KM1748 and KM1750.

11. Detection of human VEGF receptor Flt-1 by Western blotting using monoclonal antibody Cell membrane components were prepared from NIH3T3-Flt-1 cells and controls NIH3T3 cells (NIH3T3-Neo) in accordance with a known method (*Cancer Research*, 46, 4438 (1986)) and subjected to electrophoresis by the SDS-PAGE METHOD. The SDS-PAGE was carried out in accordance with a known method (*Anticancer Research*, 12, 1121 (1992)) by subjecting 15 μg, as protein per lane, of the cell membrane components to the electrophoresis using a 5 to 20% gradient gel (produced by Atto) under reducing conditions. The thus treated proteins were transferred to a PVDF membrane in accordance with a known method (*Anticancer Research*, 12, 1121, (1992)). Next, the PVDF membrane was allowed to react with PBS containing 1% BSA at room temperature for 30 minutes to effect blocking and then to react with the culture supernatant of the anti-human VEGF receptor Flt-1 monoclonal antibody KM1737 overnight at 4° C. The thus treated membrane was washed with PBS containing 0.05% Tween and then allowed to react with peroxidase-labeled goat anti-mouse IgG (5,000 times dilution: produced by Chemicon) at room temperature for 2 hours. After washing with 0.05% Tween-containing PBS, bands to which the anti-human VEGF receptor Flt-1 monoclonal antibody KM1737 was linked were detected using ECL™ Western blotting detection reagents (produced by Amersham).

Figure 10:
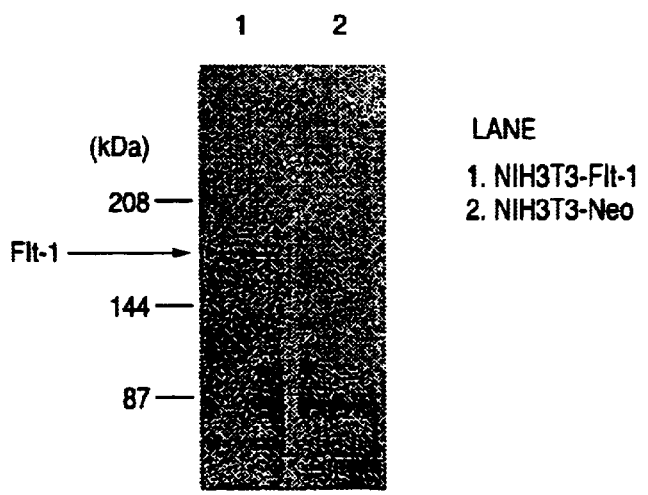
FIG. 10 is a graph showing results of the examination of the reactivity of anti-human VEGF receptor Flt-1 monoclonal antibody KM1737 with human VEGF receptor Flt-1 by Western blotting. Lane 1 shows Western blotting pattern of NIH3T3-Flt-1 cells and lane 2 shows the pattern of NIH3T3-Neo cells.

The results are shown in FIG. 10. It was confirmed that the anti-human VEGF receptor Flt-1 monoclonal antibody KM1737 can detect the human VEGF receptor Flt-1 of 180 kilo dalton in molecular weight expressed in the NIH3T3-Flt-1 cells.

12. Detection of soluble human VEGF receptor Flt-1 using monoclonal antibody

The anti-human VEGF receptor Flt-1 monoclonal antibody KM1732 was diluted was PBS to a concentration of 10 μg/ml and dispensed in 50 μl/well portions into a 96 well plate for EIA (produced by Greiner) and allowed to standard overnight at 4° C. for coating. After washing, PBS containing 1% bovine serum albumin (BSA) was dispensed in 100 μl/well portions and 1 hour of the reaction was carried out at room temperature to effect blocking of the remained active groups. After discarding 1% BSA-PBS, the purified soluble human VEGF receptors Flt-1 7N and Flt-1 3N obtained in the above-described step 1-(4) and diluted with 1% BSA-PBS to a concentration of 1,000 to 0.0056 ng/ml were allowed to react with the antibody overnight at 4° C. After washing with 0.05% Tween-PBS, the anti-human VEGF receptor Flt-1 monoclonal antibody KM1730 labeled with biotin by a known method (*Enzyme Antibody Method:* published by Gakusai Kikau, 1985) was diluted with 1% BSA-PBS to a concentration of 0.1 μg/ml and dispensed in 50 μl/well portions to carry out the reaction at room temperature for 2 hours. After washing with 0.05% Tween-PBS, avidin-labeled peroxidase (produced by Vector) diluted 4,000 times with 1% BSA-PBS was dispensed in 50 μl/well portions to carry out the reaction at room temperature for 1 hour. After washing with 0.05% Tween-PBS, color development was caused using ABTS substrate solution (2,2-azinobis(3-ethylbenzothiazole-6-sulfonic acid) ammonium salt) to measure absorbance at OD415 nm using E max (produced by Molecular Devices).

Figure 11:
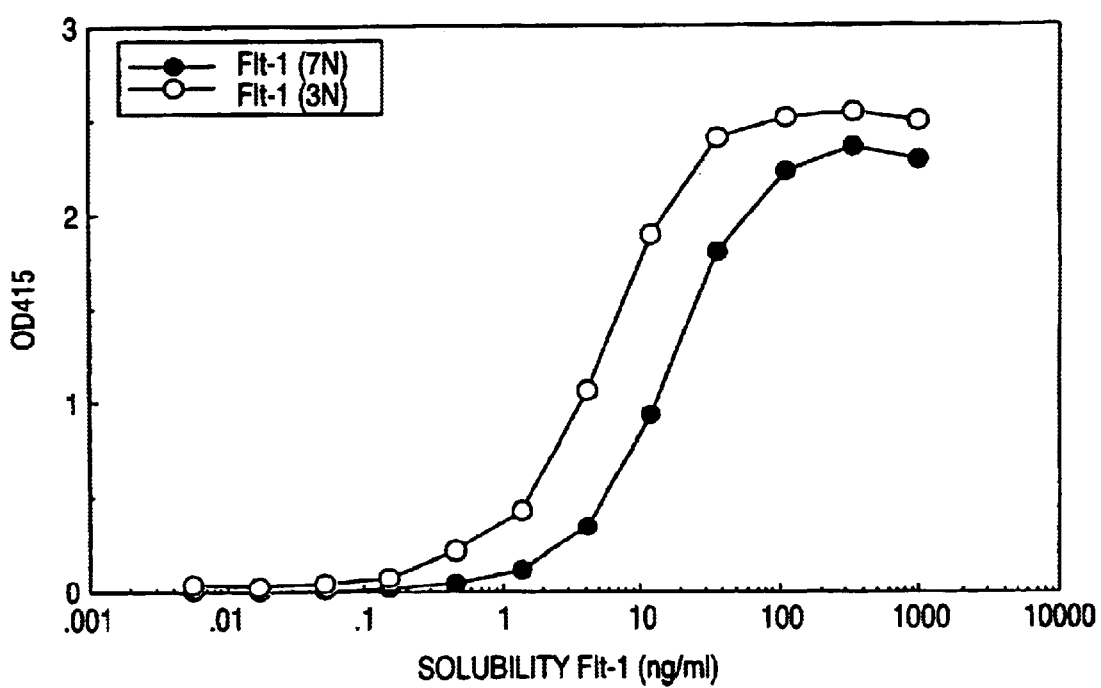
FIG. 11 is a graph showing results of the examination of the determination system of soluble human VEGF receptors Flt-1 3N and Flt-1 7N, carried out using anti-human VEGF receptor Flt-1 monoclonal antibodies KM1732 and biotinated KM1730.

The results are shown in FIG. 11. As the results, it was found that the soluble human VEGF receptors Flt-1 3N and Flt-1 7N can be measured from minimum concentrations of 0.46 ng/ml and 1.37 ng/ml, respectively, by the use of the anti-human VEGF receptor Flt-1 monoclonal antibody KM1732 and the biotin-labeled anti-human VEGF receptor Flt-1 monoclonal antibody KM1730.

13. Confirmation of the reactivity of monoclonal antibodies with human vascular endothelial cells HUVEC The reactivity of anti-human VEGF receptor Flt-1 monoclonal antibodies described in the above-described section 5 with human vascular endothelial cells HUVEC was confirmed by immunocyte staining in the following manner.

A total of $2 \times 10^5$ cells of human umbilical vein endothelial cells (HUVEC) were suspended in 100 μl of a buffer solution for immunocyte staining use (PBS containing 1% BSA, 0.02% EDTA and 0.05% sodium aside) and dispensed in a round bottom 96 well plate. After centrifugation at 4° C. and at 350×g for 1 minute, the supernatant fluid was discarded and the resulting cells were mixed with 50 μl (10 μg/ml) of each of biotinated purified antibodies KM1730 and KM1750 and control antibodies thereof, individually, and subsequently incubated at 4° C. for 30 minutes. As the control antibody of KM1730, an anti-MxA monoclonal antibody KM1135 (WO 96/05230) of IgG1 type which is the same subclass as KM1730 was used. As the control antibody of MK1750, an anti-T cell receptor γ chain monoclonal antibody KM365 (Japanese Published Unexamined Patent Application No. 491/90) of IgG2b which is the same subclass as KM1750 was used. Thereafter, 200 μl of the buffer solution for immunocyte staining use was added to each well, and the cells were washed by carrying out centrifugation at 4° C. and at 350×g for 1 minute and then the resulting supernatant was discarded. After again repeating this washing step twice, the cells were mixed with 20 μl of the buffer solution for immunocyte staining use containing 5 μg/ml in concentration of Avidin-PE (Strepoavidin-R-Phycoergythrin) (produced by Gibco), and the reaction was carried out at 4° C. for 30 minutes. After the reaction, the above-described washing step was repeated three times and then the analysis was carried out using Flow Cytometer (produced by Coulter).

Figure 12:
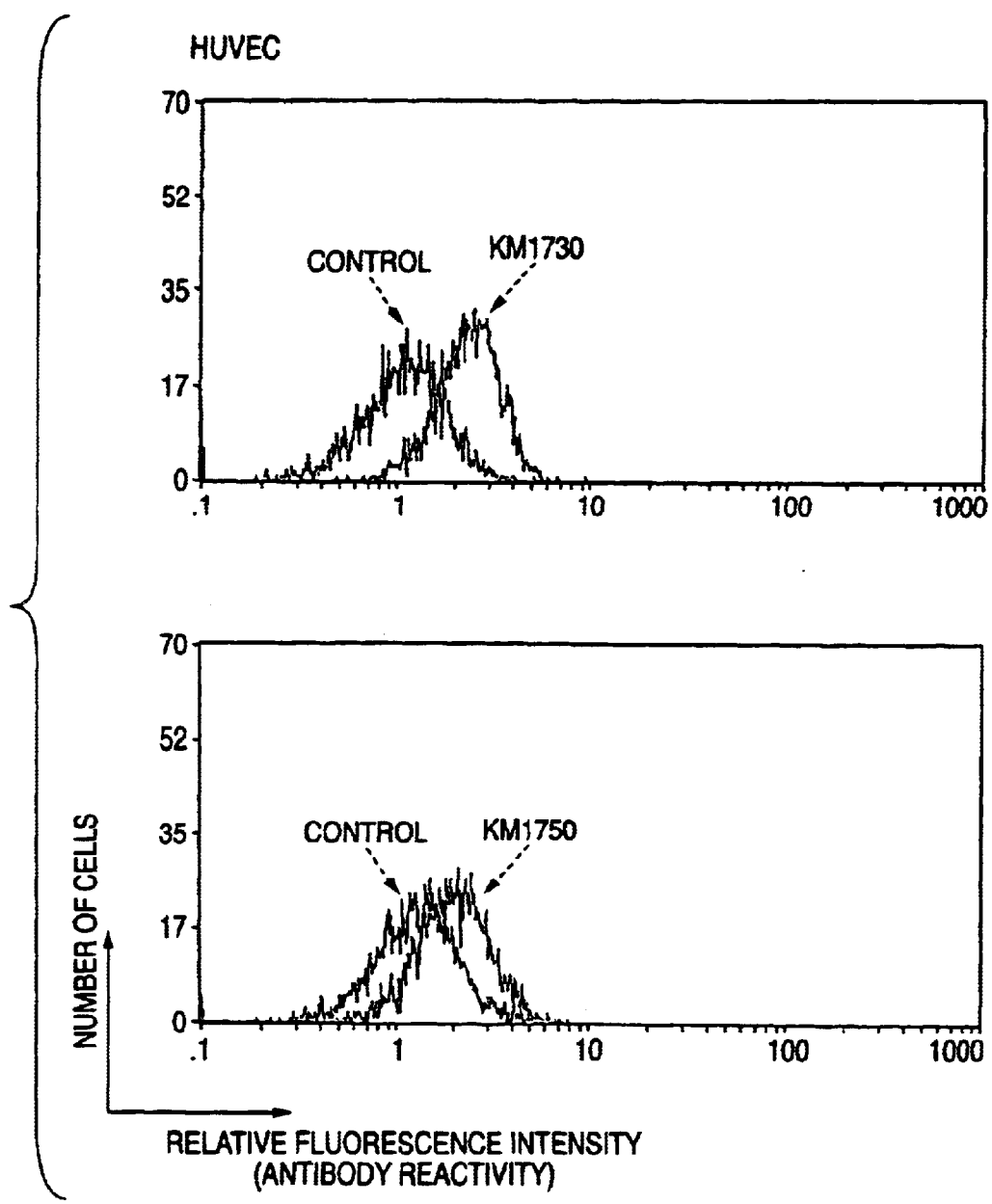
FIG. 12 is a graph showing results of the flow cytometry analysis of the reactivity of anti-human VEGF receptor Flt-1 monoclonal antibody with human vascular endothelial cells HUVEC.

The results are shown in FIG. 12. The anti-human VEGF receptor FLT-1 monoclonal antibodies KM1730 and KM1750 reacted with HUVEC when compared with their control antibodies. These results demonstrate that the monoclonal antibodies KM1730 and KM1750 can detect human VEGF receptor Flt-1 on human vascular endothelial cells.

14. Increase of the expression quantity of Flt-1 on HUVEC by VEGF stimulation

As a model of vascular endothelial cells in an angiogenesis region, changes in the expression of human VEGF receptor Flt-1 before and after stimulation with VEGF were examined using the anti-Human VEGF receptor Flt-1 monoclonal antibody KM1730 in accordance with the following procedure.

A total of 4 to $6 \times 10^5$ cells of each of four lots of HUVEC (lot #4031, #4102, #2477 and #4723; purchased from Clonetics) were suspended in 20 ml of a medium (produced by KURABO) (control medium) composed of E-BM medium further supplemented with 5% fetal bovine serum (FBS), 10 ng/ml of human recombinant type epidermal growth factor (hEGF), 1 μg/ml of hydrocortisone, 50 μg/ml of gentamicin and 50 ng/ml of amphotericin, and the suspension was further mixed with 1.2 μg/ml of bovine brain extract (BBE) (produced by KURABO) as a growth factor and subjected to 2 to 3 days of culturing at 37° C. When the cells were proliferated into 1 to $2 \times 10^6$ cells, the medium was removed and replaced with 20 ml of fresh control medium to carry out a total of 2 days of culturing. After the culturing for 1 day, human VEGF was added to a final concentration of 5 ng/ml, and the cells after the additional culturing for 1 day were used as VEGF-stimulated cells. Cells cultured for 2 days without adding VEGF were used as control cells (VEGF-non-stimulated cells). After the culturing, the cells were collected to examine reactivity of the anti-human VEGF receptor Flt-1 monoclonal antibody KM1730 by the immunocyte staining method in accordance with the procedure described in the above section 13.

Figure 13:
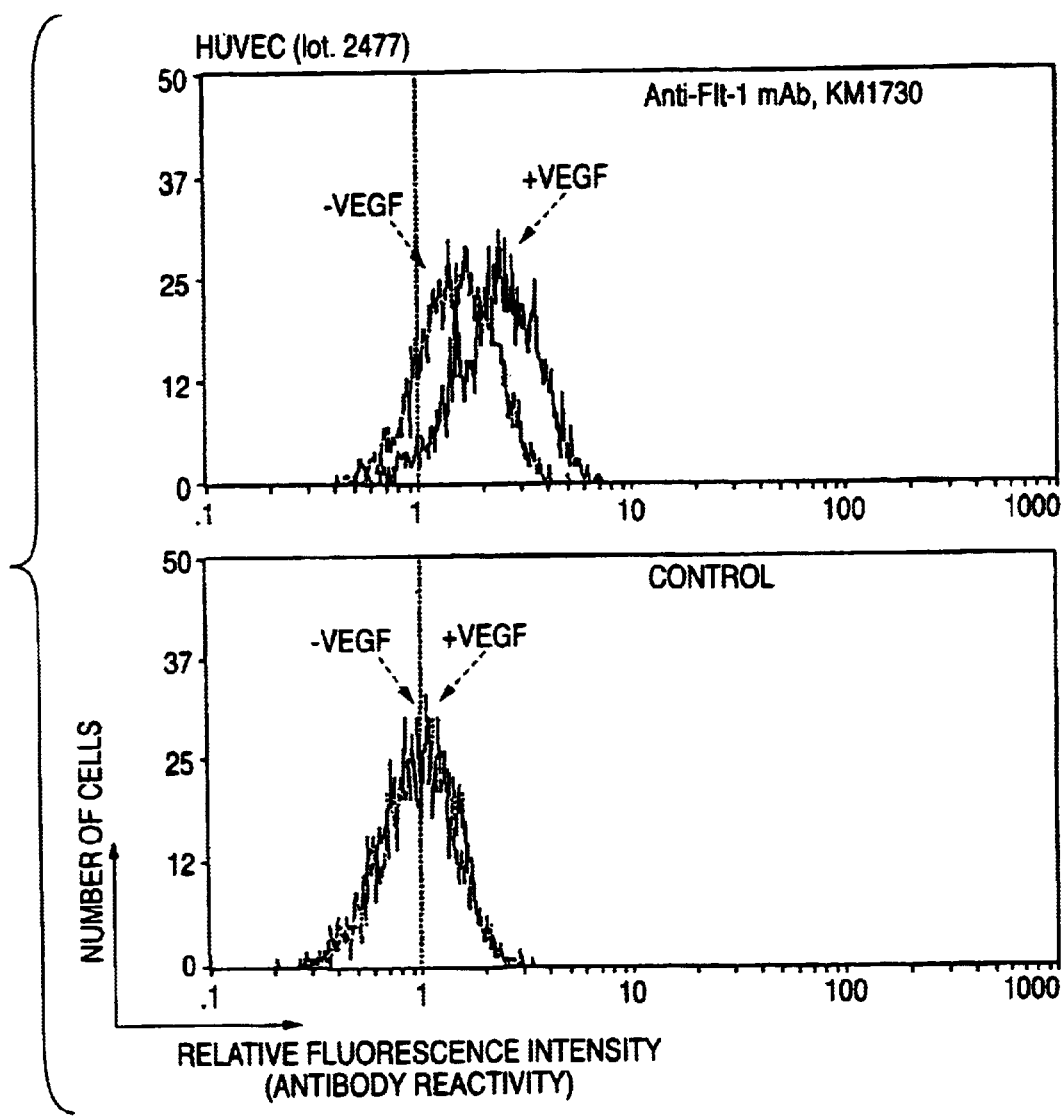
FIG. 13 is a graph showing results of the flow cytometry analysis of the reactivity of anti-human VEGF receptor Flt-1 monoclonal antibody with human vascular endothelial cells HUVEC under a VEGF non-stimulation or stimulation condition.
Figure 14:
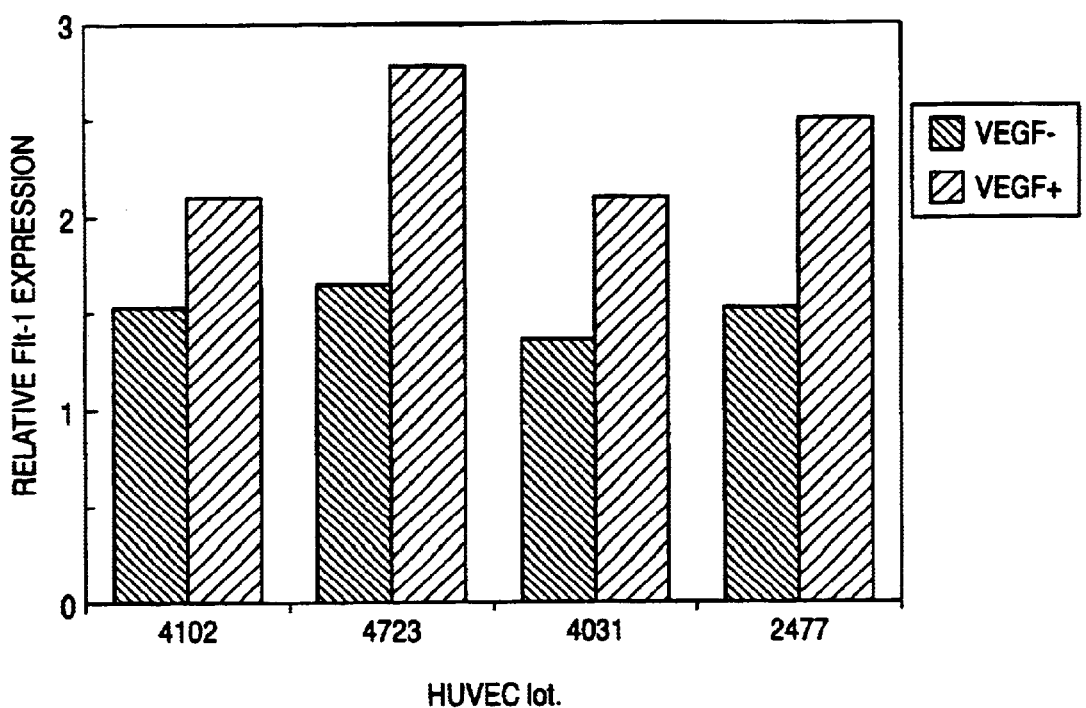
FIG. 14 is a graph showing results of the analysis on the changes in the expression quantity of human VEGF receptor Flt-1 in human vascular endothelial cells HUVEC under a VEGF non-stimulation or stimulation condition. The expression quantity of Flt-1 is shown as a relative reaction value of anti-human VEGF receptor Flt-1 monoclonal antibody KM1730 when the reactivity of a control antibody is defined as 1.

Results of the examination of its reactivity with the lot #2477 HUVEC are shown in FIG. 13. KM1730 reacted with VEGF-non-stimulated HUVEC but more strongly with VEGF-stimulated HUVEC. Reactivity of the control antibody KM1135 did not change independent of the VEGF stimulation or non-stimulation. FIG. 14 shows changes in the Flt-1 expression in four lots of HUVEC (low #4031, #4102, #2477 and #4723) by VEGF stimulation. The expression quantity of Flt-1 which can express the reactivity of KM1730 as an index is shown as a relative value when reactivity of the control antibody is defined as 1. It was revealed that all of the four lots of HUVEC can express Flt-1 by VEGF non-stimulation, and the expression quantity of Flt-1 increases by the VEGF stimulation.

The increase of the expression quantity of Flt-1 and the reactivity of anti-Flt-1 monoclonal antibody in the VEGF-stimulated human vascular endothelial cells HUVEC as a model of angiogenesis shows that the monoclonal antibody is useful for the diagnosis or treatment of diseases in which their morbid states progress by the acceleration of angiogenesis caused by VEGF, such as tumors, rheumatoid arthritis, diabetic retinopathy, and the like.

While the invention has been described in detail and with reference to specific embodiments thereof, it will be apparent to one skilled in the art that various changes and modifications can be made therein without departing from the spirit and scope thereof.

This application is based on Japanese application No. Hei B-311109 filed on Nov. 21. 1996 and International application No. PCT/JP97/04259 filed on Nov. 21, 1997, the entire contents of which are incorporated hereinto by reference.

What is claimed is:

1. A monoclonal antibody KM1730 belonging to mouse IgG1 subclass produced by hybridoma KM1730 (FERM BP-5697).

2. Hybridoma KM1730 (FERM BP-5697) which produces the monoclonal antibody of claim 1.

3. A monoclonal antibody KM1731 belonging to mouse IgG2a subclass produced by hybridoma KM1731 (FERM BP-5718).

4. Hybridoma KM1731 (FERM BP-5718) which produces the monoclonal antibody of claim 2.

5. A monoclonal antibody KM1732 belonging to mouse IgG1 subclass produced by hybridoma KM1732 (FERM BP-5698).

6. Hybridoma KB1732 (FERM BP-5698) which produces the monoclonal antibody of claim 3.

7. A monoclonal antibody KM1748 belonging to mouse IgG2b subclass produced by hybridoma KM1748 (FERM BP-5699).

8. Hybridoma KM1748 (FERM BP-5699) which produces the monoclonal antibody of claim 4.

9. A monoclonal antibody KM1750 belonging to mouse IgG2B subclass produced by hybridoma KM1750 (FERM BP-5700).

10. Hybridoma KB1750 (FERM BP-5700) which produces the monoclonal antibody of claim 5.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: TaqI-NotI
      adapter with termination codon

<400> SEQUENCE: 1
cgacaaacca atataatcta agc                                              23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: TaqI-NotI
      adapter with termination codon

<400> SEQUENCE: 2
ggccgcttag attatattgg tttgt                                            25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
ggaatctaca ttgcatagct                                                  20

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 4
ttatgcggcc gcttatcctt gaacagtgag gta                                   33

<210> SEQ ID NO 5
<211> LENGTH: 4014
<212> TYPE: DNA
```

```
<213> ORGANISM: human VEGF receptor Flt-1
<220> FEATURE:
<221> NAME/KEY: CDS
<222> LOCATION: (1)..(4014)

<400> SEQUENCE: 5 atg gtc agc tac tgg gac acc ggg gtc ctg ctg tgc gcg ctg ctc agc      48
Met Val Ser Tyr Trp Asp Thr Gly Val Leu Leu Cys Ala Leu Leu Ser
 1               5                  10                  15 tgt ctg ctt ctc aca gga tct agt tca ggt tca aaa tta aaa gat cct      96
Cys Leu Leu Leu Thr Gly Ser Ser Ser Gly Ser Lys Leu Lys Asp Pro
             20                  25                  30 gaa ctg agt tta aaa ggc acc cag cac atc atg caa gca ggc cag aca     144
Glu Leu Ser Leu Lys Gly Thr Gln His Ile Met Gln Ala Gly Gln Thr
         35                  40                  45 ctg cat ctc caa tgc agg ggg gaa gca gcc cat aaa tgg tct ttg cct     192
Leu His Leu Gln Cys Arg Gly Glu Ala Ala His Lys Trp Ser Leu Pro
     50                  55                  60 gaa atg gtg agt aag gaa agc gaa agg ctg agc ata act aaa tct gcc     240
Glu Met Val Ser Lys Glu Ser Glu Arg Leu Ser Ile Thr Lys Ser Ala
 65                  70                  75                  80 tgt gga aga aat ggc aaa caa ttc tgc agt act tta acc ttg aac aca     288
Cys Gly Arg Asn Gly Lys Gln Phe Cys Ser Thr Leu Thr Leu Asn Thr
                 85                  90                  95 gct caa gca aac cac act ggc ttc tac agc tgc aaa tat cta gct gta     336
Ala Gln Ala Asn His Thr Gly Phe Tyr Ser Cys Lys Tyr Leu Ala Val
            100                 105                 110 cct act tca aag aag aag gaa aca gaa tct gca atc tat ata ttt att     384
Pro Thr Ser Lys Lys Lys Glu Thr Glu Ser Ala Ile Tyr Ile Phe Ile
        115                 120                 125 agt gat aca ggt aga cct ttc gta gag atg tac agt gaa atc ccc gaa     432
Ser Asp Thr Gly Arg Pro Phe Val Glu Met Tyr Ser Glu Ile Pro Glu
    130                 135                 140 att ata cac atg act gaa gga agg gag ctc gtc att ccc tgc cgg gtt     480
Ile Ile His Met Thr Glu Gly Arg Glu Leu Val Ile Pro Cys Arg Val
145                 150                 155                 160 acg tca cct aac atc act gtt act tta aaa aag ttt cca ctt gac act     528
Thr Ser Pro Asn Ile Thr Val Thr Leu Lys Lys Phe Pro Leu Asp Thr
                165                 170                 175 ttg atc cct gat gga aaa cgc ata atc tgg gac agt aga aag ggc ttc     576
Leu Ile Pro Asp Gly Lys Arg Ile Ile Trp Asp Ser Arg Lys Gly Phe
            180                 185                 190 atc ata tca aat gca acg tac aaa gaa ata ggg ctt ctg acc tgt gaa     624
Ile Ile Ser Asn Ala Thr Tyr Lys Glu Ile Gly Leu Leu Thr Cys Glu
        195                 200                 205 gca aca gtc aat ggg cat ttg tat aag aca aac tat ctc aca cat cga     672
Ala Thr Val Asn Gly His Leu Tyr Lys Thr Asn Tyr Leu Thr His Arg
    210                 215                 220 caa acc aat aca atc ata gat gtc caa ata agc aca cca cgc cca gtc     720
Gln Thr Asn Thr Ile Ile Asp Val Gln Ile Ser Thr Pro Arg Pro Val
225                 230                 235                 240 aaa tta ctt aga ggc cat act ctt gtc ctc aat tgt act gct acc act     768
Lys Leu Leu Arg Gly His Thr Leu Val Leu Asn Cys Thr Ala Thr Thr
                245                 250                 255 ccc ttg aac acg aga gtt caa atg acc tgg agt tac cct gat gaa aaa     816
Pro Leu Asn Thr Arg Val Gln Met Thr Trp Ser Tyr Pro Asp Glu Lys
            260                 265                 270 aat aag aga gct tcc gta agg cga cga att gac caa agc aat tcc cat     864
Asn Lys Arg Ala Ser Val Arg Arg Arg Ile Asp Gln Ser Asn Ser His
        275                 280                 285
```

```
gcc aac ata ttc tac agt gtt ctt act att gac aaa atg cag aac aaa      912
Ala Asn Ile Phe Tyr Ser Val Leu Thr Ile Asp Lys Met Gln Asn Lys
    290                 295                 300 gac aaa gga ctt tat act tgt cgt gta agg agt gga cca tca ttc aaa      960
Asp Lys Gly Leu Tyr Thr Cys Arg Val Arg Ser Gly Pro Ser Phe Lys
305                 310                 315                 320 tct gtt aac acc tca gtg cat ata tat gat aaa gca ttc atc act gtg     1008
Ser Val Asn Thr Ser Val His Ile Tyr Asp Lys Ala Phe Ile Thr Val
                325                 330                 335 aaa cat cga aaa cag cag gtg ctt gaa acc gta gct ggc aag cgg tct     1056
Lys His Arg Lys Gln Gln Val Leu Glu Thr Val Ala Gly Lys Arg Ser
        340                 345                 350 tac cgg ctc tct atg aaa gtg aag gca ttt ccc tcg ccg gaa gtt gta     1104
Tyr Arg Leu Ser Met Lys Val Lys Ala Phe Pro Ser Pro Glu Val Val
            355                 360                 365 tgg tta aaa gat ggg tta cct gcg act gag aaa tct gct cgc tat ttg     1152
Trp Leu Lys Asp Gly Leu Pro Ala Thr Glu Lys Ser Ala Arg Tyr Leu
    370                 375                 380 act cgt ggc tac tcg tta att atc aag gac gta act gaa gag gat gca     1200
Thr Arg Gly Tyr Ser Leu Ile Ile Lys Asp Val Thr Glu Glu Asp Ala
385                 390                 395                 400 ggg aat tat aca atc ttg ctg agc ata aaa cag tca aat gtg ttt aaa     1248
Gly Asn Tyr Thr Ile Leu Leu Ser Ile Lys Gln Ser Asn Val Phe Lys
                405                 410                 415 aac ctc act gcc act cta att gtc aat gtg aaa ccc cag att tac gaa     1296
Asn Leu Thr Ala Thr Leu Ile Val Asn Val Lys Pro Gln Ile Tyr Glu
        420                 425                 430 aag gcc gtg tca tcg ttt cca gac ccg gct ctc tac cca ctg ggc agc     1344
Lys Ala Val Ser Ser Phe Pro Asp Pro Ala Leu Tyr Pro Leu Gly Ser
            435                 440                 445 aga caa atc ctg act tgt acc gca tat ggt atc cct caa cct aca atc     1392
Arg Gln Ile Leu Thr Cys Thr Ala Tyr Gly Ile Pro Gln Pro Thr Ile
    450                 455                 460 aag tgg ttc tgg cac ccc tgt aac cat aat cat tcc gaa gca agg tgt     1440
Lys Trp Phe Trp His Pro Cys Asn His Asn His Ser Glu Ala Arg Cys
465                 470                 475                 480 gac ttt tgt tcc aat aat gaa gag tcc ttt atc ctg gat gct gac agc     1488
Asp Phe Cys Ser Asn Asn Glu Glu Ser Phe Ile Leu Asp Ala Asp Ser
                485                 490                 495 aac atg gga aac aga att gag agc atc act cag cgc atg gca ata ata     1536
Asn Met Gly Asn Arg Ile Glu Ser Ile Thr Gln Arg Met Ala Ile Ile
        500                 505                 510 gaa gga aag aat aag atg gct agc acc ttg gtt gtg gct gac tct aga     1584
Glu Gly Lys Asn Lys Met Ala Ser Thr Leu Val Val Ala Asp Ser Arg
            515                 520                 525 att tct gga atc tac att tgc ata gct tcc aat aaa gtt ggg act gtg     1632
Ile Ser Gly Ile Tyr Ile Cys Ile Ala Ser Asn Lys Val Gly Thr Val
    530                 535                 540 gga aga aac ata agc ttt tat atc aca gat gtg cca aat ggg ttt cat     1680
Gly Arg Asn Ile Ser Phe Tyr Ile Thr Asp Val Pro Asn Gly Phe His
545                 550                 555                 560 gtt aac ttg gaa aaa atg ccg acg gaa gga gag gac ctg aaa ctg tct     1728
Val Asn Leu Glu Lys Met Pro Thr Glu Gly Glu Asp Leu Lys Leu Ser
                565                 570                 575 tgc aca gtt aac aag ttc tta tac aga gac gtt act tgg att tta ctg     1776
Cys Thr Val Asn Lys Phe Leu Tyr Arg Asp Val Thr Trp Ile Leu Leu
        580                 585                 590 cgg aca gtt aat aac aga aca atg cac tac agt att agc aag caa aaa     1824
Arg Thr Val Asn Asn Arg Thr Met His Tyr Ser Ile Ser Lys Gln Lys
            595                 600                 605
```

-continued

```
atg gcc atc act aag gag cac tcc atc act ctt aat ctt acc atc atg      1872
Met Ala Ile Thr Lys Glu His Ser Ile Thr Leu Asn Leu Thr Ile Met
    610             615                 620 aat gtt tcc ctg caa gat tca ggc acc tat gcc tgc aga gcc agg aat      1920
Asn Val Ser Leu Gln Asp Ser Gly Thr Tyr Ala Cys Arg Ala Arg Asn
625             630                 635                 640 gta tac aca ggg gaa gaa atc ctc cag aag aaa gaa att aca atc aga      1968
Val Tyr Thr Gly Glu Glu Ile Leu Gln Lys Lys Glu Ile Thr Ile Arg
                645                 650                 655 gat cag gaa gca cca tac ctc ctg cga aac ctc agt gat cac aca gtg      2016
Asp Gln Glu Ala Pro Tyr Leu Leu Arg Asn Leu Ser Asp His Thr Val
            660                 665                 670 gcc atc agc agt tcc acc act tta gac tgt cat gct aat ggt gtc ccc      2064
Ala Ile Ser Ser Ser Thr Thr Leu Asp Cys His Ala Asn Gly Val Pro
        675                 680                 685 gag cct cag atc act tgg ttt aaa aac aac cac aaa ata caa caa gag      2112
Glu Pro Gln Ile Thr Trp Phe Lys Asn Asn His Lys Ile Gln Gln Glu
    690                 695                 700 cct gga att att tta gga cca gga agc agc acg ctg ttt att gaa aga      2160
Pro Gly Ile Ile Leu Gly Pro Gly Ser Ser Thr Leu Phe Ile Glu Arg
705             710                 715                 720 gtc aca gaa gag gat gaa ggt gtc tat cac tgc aaa gcc acc aac cag      2208
Val Thr Glu Glu Asp Glu Gly Val Tyr His Cys Lys Ala Thr Asn Gln
                725                 730                 735 aag ggc tct gtg gaa agt tca gca tac ctc act gtt caa gga acc tcg      2256
Lys Gly Ser Val Glu Ser Ser Ala Tyr Leu Thr Val Gln Gly Thr Ser
            740                 745                 750 gac aag tct aat ctg gag ctg atc act cta aca tgc acc tgt gtg gct      2304
Asp Lys Ser Asn Leu Glu Leu Ile Thr Leu Thr Cys Thr Cys Val Ala
        755                 760                 765 gcg act ctc ttc tgg ctc cta tta acc ctc ctt atc cga aaa atg aaa      2352
Ala Thr Leu Phe Trp Leu Leu Leu Thr Leu Leu Ile Arg Lys Met Lys
    770                 775                 780 agg tct tct tct gaa ata aag act gac tac cta tca att ata atg gac      2400
Arg Ser Ser Ser Glu Ile Lys Thr Asp Tyr Leu Ser Ile Ile Met Asp
785             790                 795                 800 cca gat gaa gtt cct ttg gat gag cag tgt gag cgg ctc cct tat gat      2448
Pro Asp Glu Val Pro Leu Asp Glu Gln Cys Glu Arg Leu Pro Tyr Asp
                805                 810                 815 gcc agc aag tgg gag ttt gcc cgg gag aga ctt aaa ctg ggc aaa tca      2496
Ala Ser Lys Trp Glu Phe Ala Arg Glu Arg Leu Lys Leu Gly Lys Ser
            820                 825                 830 ctt gga aga ggg gct ttt gga aaa gtg gtt caa gca tca gca ttt ggc      2544
Leu Gly Arg Gly Ala Phe Gly Lys Val Val Gln Ala Ser Ala Phe Gly
        835                 840                 845 att aag aaa tca cct acg tgc cgg act gtg gct gtg aaa atg ctg aaa      2592
Ile Lys Lys Ser Pro Thr Cys Arg Thr Val Ala Val Lys Met Leu Lys
    850                 855                 860 gag ggg gcc acg gcc agc gag tac aaa gct ctg atg act gag cta aaa      2640
Glu Gly Ala Thr Ala Ser Glu Tyr Lys Ala Leu Met Thr Glu Leu Lys
865             870                 875                 880 atc ttg acc cac att ggc cac cat ctg aac gtg gtt aac ctg ctg gga      2688
Ile Leu Thr His Ile Gly His His Leu Asn Val Val Asn Leu Leu Gly
                885                 890                 895 gcc tgc acc aag caa gga ggg cct ctg atg gtg att gtt gaa tac tgc      2736
Ala Cys Thr Lys Gln Gly Gly Pro Leu Met Val Ile Val Glu Tyr Cys
            900                 905                 910 aaa tat gga aat ctc tcc aac tac ctc aag agc aaa cgt gac tta ttt      2784
Lys Tyr Gly Asn Leu Ser Asn Tyr Leu Lys Ser Lys Arg Asp Leu Phe
```

|  |  |
|---|---|
| ttt ctc aac aag gat gca gca cta cac atg gag cct aag aaa gaa aaa<br>Phe Leu Asn Lys Asp Ala Ala Leu His Met Glu Pro Lys Lys Glu Lys<br>    930                      935                    940 | 2832 |
| atg gag cca ggc ctg gaa caa ggc aag aaa cca aga cta gat agc gtc<br>Met Glu Pro Gly Leu Glu Gln Gly Lys Lys Pro Arg Leu Asp Ser Val<br>945                      950                    955                    960 | 2880 |
| acc agc agc gaa agc ttt gcg agc tcc ggc ttt cag gaa gat aaa agt<br>Thr Ser Ser Glu Ser Phe Ala Ser Ser Gly Phe Gln Glu Asp Lys Ser<br>                      965                    970                    975 | 2928 |
| ctg agt gat gtt gag gaa gag gag gat tct gac ggt ttc tac aag gag<br>Leu Ser Asp Val Glu Glu Glu Glu Asp Ser Asp Gly Phe Tyr Lys Glu<br>    980                      985                    990 | 2976 |
| ccc atc act atg gaa gat ctg att tct tac agt ttt caa gtg gcc aga<br>Pro Ile Thr Met Glu Asp Leu Ile Ser Tyr Ser Phe Gln Val Ala Arg<br>995                      1000                 1005 | 3024 |
| ggc atg gag ttc ctg tct tcc aga aag tgc att cat cgg gac ctg gca<br>Gly Met Glu Phe Leu Ser Ser Arg Lys Cys Ile His Arg Asp Leu Ala<br>1010                 1015                1020 | 3072 |
| gcg aga aac att ctt tta tct gag aac aac gtg gtg aag att tgt gat<br>Ala Arg Asn Ile Leu Leu Ser Glu Asn Asn Val Val Lys Ile Cys Asp<br>1025               1030                1035                1040 | 3120 |
| ttt ggc ctt gcc cgg gat att tat aag aac ccc gat tat gtg aga aaa<br>Phe Gly Leu Ala Arg Asp Ile Tyr Lys Asn Pro Asp Tyr Val Arg Lys<br>                    1045                1050                1055 | 3168 |
| gga gat act cga ctt cct ctg aaa tgg atg gct ccc gaa tct atc ttt<br>Gly Asp Thr Arg Leu Pro Leu Lys Trp Met Ala Pro Glu Ser Ile Phe<br>           1060                1065                1070 | 3216 |
| gac aaa atc tac agc acc aag agc gac gtg tgg tct tac gga gta ttg<br>Asp Lys Ile Tyr Ser Thr Lys Ser Asp Val Trp Ser Tyr Gly Val Leu<br>1075               1080                1085 | 3264 |
| ctg tgg gaa atc ttc tcc tta ggt ggg tct cca tac cca gga gta caa<br>Leu Trp Glu Ile Phe Ser Leu Gly Gly Ser Pro Tyr Pro Gly Val Gln<br>    1090                      1095                1100 | 3312 |
| atg gat gag gac ttt tgc agt cgc ctg agg gaa ggc atg agg atg aga<br>Met Asp Glu Asp Phe Cys Ser Arg Leu Arg Glu Gly Met Arg Met Arg<br>1105               1110                1115                1120 | 3360 |
| gct cct gag tac tct act cct gaa atc tat cag atc atg ctg gac tgc<br>Ala Pro Glu Tyr Ser Thr Pro Glu Ile Tyr Gln Ile Met Leu Asp Cys<br>                    1125                1130                1135 | 3408 |
| tgg cac aga gac cca aaa gaa agg cca aga ttt gca gaa ctt gtg gaa<br>Trp His Arg Asp Pro Lys Glu Arg Pro Arg Phe Ala Glu Leu Val Glu<br>           1140                1145                1150 | 3456 |
| aaa cta ggt gat ttg ctt caa gca aat gta caa cag gat ggt aaa gac<br>Lys Leu Gly Asp Leu Leu Gln Ala Asn Val Gln Gln Asp Gly Lys Asp<br>                    1155                1160                1165 | 3504 |
| tac atc cca atc aat gcc ata ctg aca gga aat agt ggg ttt aca tac<br>Tyr Ile Pro Ile Asn Ala Ile Leu Thr Gly Asn Ser Gly Phe Thr Tyr<br>    1170                      1175                1180 | 3552 |
| tca act cct gcc ttc tct gag gac ttc ttc aag gaa agt att tca gct<br>Ser Thr Pro Ala Phe Ser Glu Asp Phe Phe Lys Glu Ser Ile Ser Ala<br>1185               1190                1195                1200 | 3600 |
| ccg aag ttt aat tca gga agc tct gat gat gtc aga tat gta aat gct<br>Pro Lys Phe Asn Ser Gly Ser Ser Asp Asp Val Arg Tyr Val Asn Ala<br>                    1205                1210                1215 | 3648 |
| ttc aag ttc atg agc ctg gaa aga atc aaa acc ttt gaa gaa ctt tta<br>Phe Lys Phe Met Ser Leu Glu Arg Ile Lys Thr Phe Glu Glu Leu Leu<br>           1220                1225                1230 | 3696 |
| ccg aat gcc acc tcc atg ttt gat gac tac cag ggc gac agc agc act | 3744 |

```
                                                                        3792
Pro Asn Ala Thr Ser Met Phe Asp Asp Tyr Gln Gly Asp Ser Ser Thr
    1235                1240                1245 ctg ttg gcc tct ccc atg ctg aag cgc ttc acc tgg act gac agc aaa        3792
Leu Leu Ala Ser Pro Met Leu Lys Arg Phe Thr Trp Thr Asp Ser Lys
    1250                1255                1260 ccc aag gcc tcg ctc aag att gac ttg aga gta acc agt aaa agt aag        3840
Pro Lys Ala Ser Leu Lys Ile Asp Leu Arg Val Thr Ser Lys Ser Lys
1265                1270                1275                1280 gag tcg ggg ctg tct gat gtc agc agg ccc agt ttc tgc cat tcc agc        3888
Glu Ser Gly Leu Ser Asp Val Ser Arg Pro Ser Phe Cys His Ser Ser
                1285                1290                1295 tgt ggg cac gtc agc gaa ggc aag cgc agg ttc acc tac gac cac gct        3936
Cys Gly His Val Ser Glu Gly Lys Arg Arg Phe Thr Tyr Asp His Ala
            1300                1305                1310 gag ctg gaa agg aaa atc gcg tgc tgc tcc ccg ccc cca gac tac aac        3984
Glu Leu Glu Arg Lys Ile Ala Cys Cys Ser Pro Pro Pro Asp Tyr Asn
        1315                1320                1325 tcg gtg gtc ctg tac tcc acc cca ccc atc                                4014
Ser Val Val Leu Tyr Ser Thr Pro Pro Ile
    1330                1335

<210> SEQ ID NO 6
<211> LENGTH: 1338
<212> TYPE: PRT
<213> ORGANISM: human VEGF receptor Flt-1

<400> SEQUENCE: 6

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

-continued

```
Lys Leu Leu Arg Gly His Thr Leu Val Leu Asn Cys Thr Ala Thr Thr
            245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
            275                 280                 285
Ala Asn Ile Phe Tyr Ser Val Leu Thr Ile Asp Lys Met Gln Asn Lys
            290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                    325                 330                 335
Lys His Arg Lys Gln Gln Val Leu Glu Thr Val Ala Gly Lys Arg Ser
                    340                 345                 350
Tyr Arg Leu Ser Met Lys Val Lys Ala Phe Pro Ser Pro Glu Val Val
                    355                 360                 365
Trp Leu Lys Asp Gly Leu Pro Ala Thr Glu Lys Ser Ala Arg Tyr Leu
            370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                    405                 410                 415
Asn Leu Thr Ala Thr Leu Ile Val Asn Val Lys Pro Gln Ile Tyr Glu
                    420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
            450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                    485                 490                 495
Asn Met Gly Asn Arg Ile Glu Ser Ile Thr Gln Arg Met Ala Ile Ile
                    500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                    565                 570                 575
Cys Thr Val Asn Lys Phe Leu Tyr Arg Asp Val Thr Trp Ile Leu Leu
                    580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
            610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                    645                 650                 655
```

-continued

```
Asp Gln Glu Ala Pro Tyr Leu Leu Arg Asn Leu Ser Asp His Thr Val
            660                 665                 670

Ala Ile Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Leu Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu Ala
    1010                1015                1020

Ala Arg Asn Ile Leu Leu Ser Glu Asn Asn Val Val Lys Ile Cys Asp
1025                1030                1035                1040

Phe Gly Leu Ala Arg Asp Ile Tyr Lys Asn Pro Asp Tyr Val Arg Lys
                1045                1050                1055

Gly Asp Thr Arg Leu Pro Leu Lys Trp Met Ala Pro Glu Ser Ile Phe
            1060                1065                1070

Asp Lys Ile Tyr Ser Thr Lys Ser Asp Val Trp Ser Tyr Gly Val Leu
```

-continued

```
                1075                1080                1085
Leu Trp Glu Ile Phe Ser Leu Gly Gly Ser Pro Tyr Pro Gly Val Gln
        1090                1095                1100

Met Asp Glu Asp Phe Cys Ser Arg Leu Arg Glu Gly Met Arg Met Arg
1105                1110                1115                1120

Ala Pro Glu Tyr Ser Thr Pro Glu Ile Tyr Gln Ile Met Leu Asp Cys
                1125                1130                1135

Trp His Arg Asp Pro Lys Glu Arg Pro Arg Phe Ala Glu Leu Val Glu
        1140                1145                1150

Lys Leu Gly Asp Leu Leu Gln Ala Asn Val Gln Gln Asp Gly Lys Asp
        1155                1160                1165

Tyr Ile Pro Ile Asn Ala Ile Leu Thr Gly Asn Ser Gly Phe Thr Tyr
    1170                1175                1180

Ser Thr Pro Ala Phe Ser Glu Asp Phe Phe Lys Glu Ser Ile Ser Ala
1185                1190                1195                1200

Pro Lys Phe Asn Ser Gly Ser Ser Asp Asp Val Arg Tyr Val Asn Ala
                1205                1210                1215

Phe Lys Phe Met Ser Leu Glu Arg Ile Lys Thr Phe Glu Glu Leu Leu
                1220                1225                1230

Pro Asn Ala Thr Ser Met Phe Asp Asp Tyr Gln Gly Asp Ser Ser Thr
        1235                1240                1245

Leu Leu Ala Ser Pro Met Leu Lys Arg Phe Thr Trp Thr Asp Ser Lys
        1250                1255                1260

Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
                1285                1290                1295

Cys Gly His Val Ser Glu Gly Lys Arg Arg Phe Thr Tyr Asp His Ala
        1300                1305                1310

Glu Leu Glu Arg Lys Ile Ala Cys Cys Ser Pro Pro Asp Tyr Asn
        1315                1320                1325

Ser Val Val Leu Tyr Ser Thr Pro Pro Ile
    1330                1335
```